United States Patent
Singamaneni et al.

(10) Patent No.: US 9,410,949 B2
(45) Date of Patent: Aug. 9, 2016

(54) LABEL-FREE DETECTION OF RENAL CANCER

(75) Inventors: Srikanth Singamaneni, St. Louis, MO (US); Evan Kharasch, St. Louis, MO (US); Jeremiah J. Morrissey, St. Louis, MO (US); Chang Hee Lee, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 663 days.

(21) Appl. No.: 13/309,852

(22) Filed: Dec. 2, 2011

(65) Prior Publication Data

US 2012/0184451 A1 Jul. 19, 2012

Related U.S. Application Data

(60) Provisional application No. 61/419,573, filed on Dec. 3, 2010, provisional application No. 61/487,441, filed on May 18, 2011.

(51) Int. Cl.

| | | |
|---|---|---|
| G01N 33/551 | (2006.01) | |
| G01N 33/543 | (2006.01) | |
| B82Y 5/00 | (2011.01) | |
| B82Y 15/00 | (2011.01) | |
| B82Y 20/00 | (2011.01) | |
| G01N 33/574 | (2006.01) | |
| B82Y 40/00 | (2011.01) | |
| G01N 21/552 | (2014.01) | |
| G01N 21/65 | (2006.01) | |

(52) U.S. Cl.
CPC .............. *G01N 33/54346* (2013.01); *B82Y 5/00* (2013.01); *B82Y 15/00* (2013.01); *B82Y 20/00* (2013.01); *B82Y 40/00* (2013.01); *G01N 21/554* (2013.01); *G01N 21/658* (2013.01); *G01N 33/54373* (2013.01); *G01N 33/57438* (2013.01); *G01N 2201/02* (2013.01)

(58) Field of Classification Search
None
See application file for complete search history.

(56) References Cited

U.S. PATENT DOCUMENTS

| | | | |
|---|---|---|---|
| 4,674,878 A | 6/1987 | Vo-Dinh | |
| 7,651,863 B2 | 1/2010 | Hulteen et al. | |
| 7,704,754 B2* | 4/2010 | Malak | A61L 2/08 436/524 |
| 7,803,574 B2* | 9/2010 | Desai | A61L 27/54 424/432 |
| 2003/0227628 A1 | 12/2003 | Kreimer et al. | |
| 2007/0015288 A1 | 1/2007 | Hulteen et al. | |
| 2007/0140900 A1 | 6/2007 | Wang et al. | |
| 2008/0118986 A1 | 5/2008 | Burrell et al. | |

OTHER PUBLICATIONS

Ishakawa et al., "Preparation of Ag particle-doped cellulose acetate gel membrane as a surface-enhanced Raman scattering active substance", Vibrational Spectroscopy, 8:445-449 (1995).*

Ishikawa et al., "Preparation of Ag particle-doped cellulose acetate gel membrane as a surface-enhanced Raman scattering active substance", Vibrational Spectroscopy, 8:445-449 (1995).*

(Continued)

*Primary Examiner* — Christopher L Chin
(74) *Attorney, Agent, or Firm* — Stinson Leonard Street LLP

(57) ABSTRACT

Natural and/or synthetic antibodies for specific proteins are adhered to nanoparticles. The nanoparticles are adhered to a substrate and the substrate is exposed to a sample that may contain the specific proteins. The substrates are then tested with surface enhanced Raman scattering techniques and/or localized surface plasmon resonance techniques to quantify the amount of the specific protein in the sample.

8 Claims, 21 Drawing Sheets

(56) References Cited

OTHER PUBLICATIONS

Yun, et al., "Linker-Molecule-Free Gold Nanorod Layer-by-Layer Films for Surface Enhanced Raman Scattering", Analytical Chemistry, vol. 79, p. 8584-8589 (2007).*

Sau et al., "Properties and Applications of Colloidal Nonspherical Noble Metal Nanoparticles", Advanced Materials, vol. 22, p. 1805-1825, (available online Jan. 4, 2010).*

Lee et al, "Improved Localized Surface Plasmon Resonance Immunoassay with Gold Bipyramid Substrates", Anal. Chem., 2009, 81, 4450-4455.*

* cited by examiner

LABEL-FREE DETECTION OF RENAL CANCER

CROSS REFERENCE TO RELATED APPLICATIONS

This application claims the benefit of U.S. Provisional Patent Application No. 61/419,573 filed Dec. 3, 2010 and U.S. Provisional Patent Application No. 61/487,441 filed May 18, 2011, which are both hereby incorporated by reference in their entirety.

STATEMENT REGARDING FEDERALLY SPONSORED RESEARCH OR DEVELOPMENT

This invention was made with government support under W81XWH-11-1- 0439 awarded by the United States Army. The Government has certain rights in the invention.

BACKGROUND

The embodiments described herein relate generally to label-free detection of renal cancer and, more particularly, to a method and a system for detecting the presence of predetermined proteins via surface enhanced Raman scattering (SERS) or localized surface plasmon resonance. In one embodiment, the predetermined proteins are indicative of renal cancer (e.g., kidney cancer) and a patient's urine is tested for the presence of the predetermined proteins.

Renal cancer (e.g., kidney cancer) is generally silent, frequently fatal, and accounts for 3% of adult malignancies. In the United States in 2009, more than 57,000 cases of kidney cancer were diagnosed, and almost 13,000 deaths occurred that were attributable to this disease. Altogether, this disease represents the sixth leading cause of death due to cancer. According to the SEER Stat Facts of the Kidney Cancer Homepage of the National Cancer Institute, one in 70 adults in the United States will develop kidney cancer during their lifetime. For men, renal cancer is seventh among newly diagnosed cancers in 2009, ahead of both leukemia and pancreatic cancer. For women it is eighth in newly diagnosed cancers, ahead of both ovarian and pancreatic cancer. Renal cancer, when symptomatically diagnosed by the classic triad of flank pain, hematuria and a palpable flank mass, has already metastasized to lymph nodes or other organs in 30-40% of patients. Renal cancer is resistant to chemotherapy, and metastatic disease portends a miserable prognosis.

There are substantial benefits to early detection. If, at diagnosis, the tumor is confined within the renal capsule, survival rates can exceed 70%. Additional benefits of early detection include the opportunities for laparoscopic, as opposed to open, nephrectomy and partial, as opposed to total, nephrectomy. Minimally invasive laparoscopic surgery rather than open laparotomy enables shorter hospitalization, faster recovery, less pain and disability, fewer complications and lower cost. Nephron-sparing partial nephrectomy rather than total nephrectomy preserves renal mass and long-term renal function. Partial nephrectomy is associated with better long-term survival of patients with stage T1b tumors than patients who undergo radical nephrectomy, suggesting that conventional open radical nephrectomy may be considered over-treatment. The desire to preserve renal function and to minimize future chronic kidney disease are compelling factors for early diagnosis of renal cancer. Identifying suitable biomarkers of kidney cancer and development of efficient technology to rapidly and noninvasively detect these biomarkers are important to disease diagnosis and documenting response to therapy.

Kidney cancer causing carcinogens such as trichloroethylene (TCE) are ubiquitously used in industrial and military applications as a degreaser. TCE is a highly toxic industrial solvent and a common contaminant in soil and groundwater at over 1200 sites across the United States, including hundreds of military bases—most prominently Camp Lejeune, N.C., the largest TCE contamination site in the country. Smoking and obesity, also common in military communities, are also risk factors for kidney cancer. Therefore kidney cancer, itself common in the civilian population, is an even greater threat to the health of the military communities, which constitute an at-risk population numbering in the millions. Kidney cancer is a deadly stealth killer, growing silently and undetected, until so large, advanced, and usually metastatic, that symptoms occur. Such cancers are fatal in 95% of the victims. In contrast, if detected early, kidney cancer can be cured in over 70% of the patients. Early detection also enables noninvasive surgery, quick recovery, preserving kidney function, reduction in total cost of care and minimizing disability and loss of worker productivity. There is presently no means to screen at-risk military or associated populations (indeed any population) for kidney cancer.

SERS involves dramatic enhancement (up to $10^{12}$ times or more) of the intensity of the Raman scattering from the analyte adsorbed on or in proximity to a metal surface with nanoscale roughness due primarily to the enhanced electromagnetic field. Electromagnetic enhancement depends on numerous factors such as distance of the analyte from the metal nanostructure, distance between the nanostructures in the case of dimers and aggregates, size and shape of the nanostructures, composition of the metal, and the excitation wavelength with respect to the plasmon resonance of the metal nanostructures. SERS is a powerful platform for label and label-free biosensing of a wide variety of biomolecules. There are numerous advantages to SERS based biosensors over conventional bioassays such as ELISA, Western blotting and immuno precipitation. The molecule-specific Raman bands (forming a molecular fingerprint) combined with the molecular recognition capability of the capture antibodies immobilized on the metal nanostructure surface enables the label-free detection of the target biomolecules, as described herein. Furthermore, the inherently narrow Raman bands (as opposed to broad fluorescence bands of the other techniques) enable multiplexed detection of multiple analytes in a complex mixture. Prior art SERS systems have poor sensitivity due to the poor light-metal nanostructure interaction. In addition, one often overlooked consideration in the design of SERS substrates for trace detection is the efficiency of sample collection. Known designs based on rigid substrates such as silicon, alumina, and glass resist conformal contact with the surface under investigation, making the sample collection inefficient. Accordingly, SERS substrate designs which enable efficient guiding of the incident and scattered photons complemented with easy access to analytes and their selective binding to enable reliable real-world biological sensors are desirable.

BRIEF DESCRIPTION

In one aspect, a simple and inexpensive urine test can be performed in physician's office for the detection of kidney cancer at a very early stage. The test measures the quantity of two different proteins (namely aquaporin-1 and adipophilin) present in the urine of a person. Higher amounts of these proteins are present in the urine of persons with kidney cancer compared to healthy volunteers. However, detection of these proteins using prior methods is expensive and time consuming. Aspects of the present disclosure enable an inexpensive technology to quickly measure the quantities of these proteins. The process is based on surface enhanced Raman spectroscopic (light based) and/or localized surface plasmon resonance methods which read the fingerprint of the proteins and allow measuring the exact amount of these proteins in the urine. To achieve such detection technology a novel platform, which enhances the fingerprint and makes it distinct from the noise associated with the irrelevant proteins and other molecules present in the urine, is provided.

Aspects of the disclosure can also be readily extended to the detection of various other biomolecules in physiological liquids (e.g. blood, serum, urine). Aspects of this disclosure also provide insight into the unique properties of the nanomaterials employed in this novel sensing platform. The sensitivity of this molecular fingerprint reading technology varies based on the design of the substrate comprised of nanomaterials, which can efficiently guide the incident light to hotspots, where maximum enhancement of the signal can be attained. Aspects of the disclosure create a framework for a novel design of such substrates, which are significantly better than existing designs, which have poor sensitivity and reproducibility.

Aquaporin-1 (AQP1) and adipophilin (ADFP) proteins in urine are excellent candidates for the non-invasive and early detection of renal cell carcinoma (RCC). One aspect of the present disclosure demonstrates a novel plasmonic biosensor based on metal nanostructures with imprinted artificial receptors (using molecular imprinting approach) for non-invasive and rapid screening of kidney cancer. The disclosed label-free assay is based on the detection of AQP1 and ADFP proteins in the urine using localized surface plasmon resonance (LSPR) and/or surface enhanced Raman scattering (SERS) as transduction platforms. Embodiments of the disclosure include (i) a paper based plasmonic biosensor for sensitive and specific detection of target proteins in urine for rapid screening of kidney cancer, (ii) integrating molecular imprinting with plasmonic nanostructures to overcome issues hindering the progress of plasmonic biosensors to real-world application, and (iii) the application of surface force spectroscopy to probe the specific recognition of synthetic receptors, which provides single molecule level understanding of the binding event.

In one aspect, the disclosure is related to the quantitative detection of kidney cancer biomarkers (proteins aquaporin-1 and adipophilin) in urine using localized surface Plasmon resonance (LSPR) and surface enhanced Raman scattering (SERS) as techniques to measure these biomarkers. LSPR based methodology may use both glass and paper substrates while the SERS based method may be employed using either 2D paper based substrates, or 3D substrates involving vertically aligned nanowires or any other SERS substrates. These systems and methods described herein involve the use of either natural or synthetic antibodies for capturing the proteins from urine.

Aspects of the present disclosure enable effective and inexpensive screening of large populations of current and former military personnel, their dependents, contractors, and civilians, including civilians near military bases, resulting in improved well-being of individuals developing kidney cancer, and reduced health care costs. Aspects of the invention further enable a rapid, simple, noninvasive, sensitive and specific urine test for kidney cancer, which can be used to effectively and inexpensively screen large populations of current and former military personnel, their dependents, contractors, and civilians, including civilians near military bases. Moreover, such a test can also be used to cost-effectively and noninvasively monitor and detect recurrence of kidney cancer.

A SERS substrate based on filter paper adsorbed with gold nanorods, which allows conformal contact with real-world surfaces, thus dramatically enhancing the sample collection efficiency compared to conventional rigid substrates, is provided. The hierarchical fibrous structure of paper serves as a 3D vasculature for improved uptake and transport of the analytes to the electromagnetic hot spots in the paper. The highly efficient and cost effective SERS substrates disclosed herein bring SERS-based trace detection closer to real-world applications.

BRIEF DESCRIPTION OF THE DRAWINGS

The embodiments described herein may be better understood by referring to the following description in conjunction with the accompanying drawings.

DETAILED DESCRIPTION OF THE DRAWINGS

Figure 1:
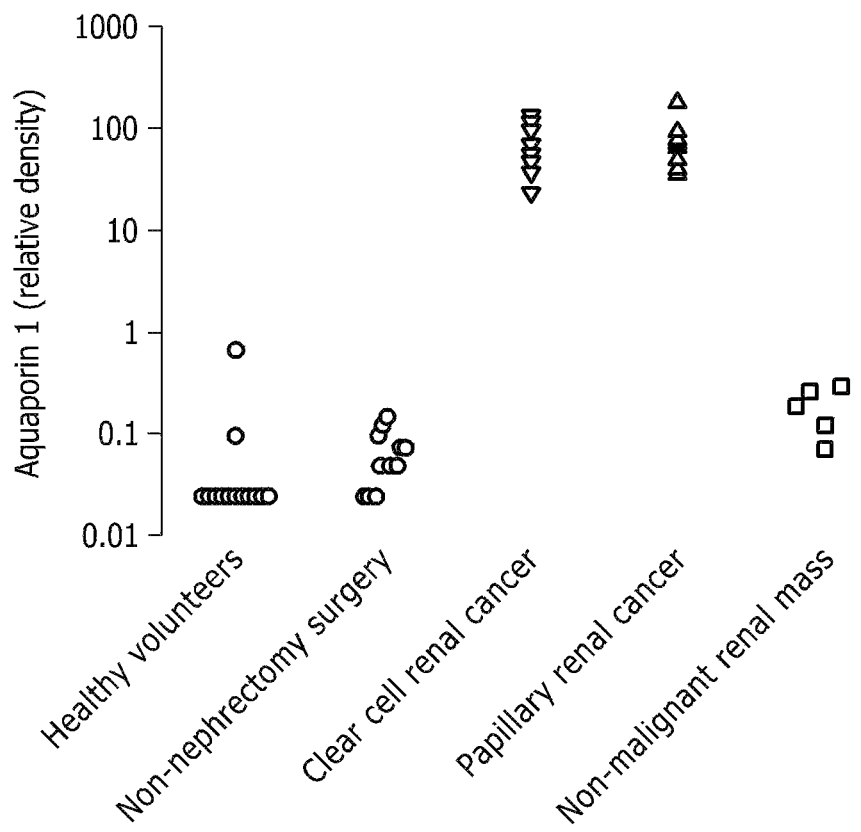
FIG. 1 is a graph of urine AQP1 concentrations in patients with and without renal cancer versus healthy control patients.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

While the detection of certain proteins indicative of renal cancer is discussed throughout, it should be appreciated that the methods and apparatuses described herein may be used in detecting other proteins or in detecting other substances in entirely different contexts. For example, although most prior studies clearly demonstrate that SERS substrates hosting closely separated metal nanostructures and/or sharp tips result in large enhancements, cost and the ease and efficiency of the sample collection are often overlooked. In real-world applications, such as explosive detection, the efficiency of sample collection becomes a decisive factor. For example, in the case of explosives such as trinitrotoluene (TNT), which inherently have low vapor pressure (~10 ppbv at room temperature), intentional packaging further lowers the actual vapor concentration by more than an order of magnitude. For detection of such explosives, it is extremely important to collect particulates (few μg), that are invariably present on the surface of objects exposed to the explosive. Physical swabbing, puffer systems (aerodynamic), and direct vapor sniffing are efficient methods to collect trace amounts of analytes. In particular, swabbing the surface under investigation with a soft and flexible substrate (swab) is a highly practical and efficient method to maximize the sample collection from a real-world surface. This strategy is being extensively employed for passenger screening at airports using ion mobility spectroscopy which involves swabbing a surface with a collector material and then performing ion spectroscopy on the swab and any particles on the swab. On the contrary, conventional SERS substrates based on silicon, glass, and porous alumina, which are conceived for homeland security applications, are not compatible with such efficient sample collection process due to their non-conformal, rigid and brittle nature.

A highly efficient paper-based SERS substrate may be fabricated by loading gold nanorods (AuNR) in a commercially available laboratory filter paper, such as a Whatman No. 1 grade, in accordance with the principles described herein. The SERS substrate described herein may be used by swabbing the surface of an object suspected of exposure to a hazardous material and analyzed via SERS. The detection of less than 140 pg of 1,4-benzenedithiol (1,4-BDT) residue spread over 4 $cm^2$ surface by swabbing the AuNR loaded paper on the surface is demonstrated herein. Previous attempts employing filter paper exhibited limited sensitivity possibly due to the thin metal films (thermally evaporated or sputtered) or poor control over the size and shape of the metal nanostructures employed in these designs. Apart from the large enhancement, the uniform decoration of the nanorods demonstrated herein preserves the favorable attributes such as flexibility, conformal nature, and capillarity of the paper. These benefits and applications, as well as many others, are contemplated as flowing from this disclosure in addition to the exemplary application of renal cancer detection.

The proteins adipophilin (ADFP) and aquaporin-1 (AQP1) in urine form excellent candidates for the noninvasive and early detection of renal cancer carcinoma (RCC). FIG. 1 shows the AQP1 concentration in patients with and without renal cancer, and healthy controls as determined by western blot analysis, expressed in arbitrary density units and normalized to urine creatinine concentration. The plot clearly shows that the concentrations of AQP1 in the urine of patients with either clear cell or papillary carcinoma were significantly greater and clearly separated from those in the non-RCC surgical control patients and the healthy individuals. Very similar results were found for ADFP. While these data clearly demonstrated the possibility of using these proteins as potential biomarkers for early detection of RCC, absolute quantification of these proteins, together with the development of an inexpensive high throughput technology, is required to advance these findings. Conventional labeled assays such as enzyme-linked immunosorbent assay (ELISA) are time-consuming, expensive and require tedious labeling procedures. These considerations clearly suggest the need for a label-free approach for rapid and quantitative detection of the proteins in urine at physiologically relevant concentrations (ng/ml), as disclosed herein.

Point of care urinalysis enabling rapid screening for kidney cancer is a novel paradigm in the early detection and recurrence monitoring of kidney cancer. A novel 3D SERS substrate comprised of vertically aligned ZnO nanorods decorated with metal (e.g., a noble metal such as gold) nanoparticles with high and reproducible SERS enhancement for the quantitative detection of the protein biomarkers in urine is disclosed herein. The vertically aligned nanowires act as waveguides for the incident and Raman scattered light. As the incident light trapped inside the nanorods traverses along the length of the nanorods, it excites surface plasmons in the metal nanostructures adsorbed on the ZnO nanowires, thereby resulting in enhanced Raman scattering of the analytes adsorbed on the metal nanostructures (see FIG. 2). The disclosed design of the SERS substrate provides distinct advantages over the conventional 2D substrates, including, but not limited to: (i) efficient interaction of light with the metal nanoparticles decorated on the nanowires, as the light traverses through the entire length of the nanowires, (ii) multiple reflections of the light in the waveguide will result in enhanced probability of exciting the electromagnetic hot spots, (iii) porous nature of the SERS substrate (interstices between the nanowires) provides efficient access to the analytes, (iv) high surface area of the nanowires results in large dynamic range of the chemical and biological sensors, and (v) facile fabrication will enable efficient, robust, reliable, and cost-effective SERS substrates for highly sensitive and selective chemical and biological sensing.

Aspects of the disclosure provide a novel, label-free assay based on the detection of ADFP and AQP1 proteins in the urine using SERS for point of care and noninvasive detection of RCC. Aspects of the present disclosure also identify characteristic Raman bands of target proteins (ADFP and AQP1) and their capture antibodies (anti-AQP1 and anti-ADFP)

using normal Raman spectroscopy or conventional 2D SERS substrates using high concentration of the antibody and protein. Aspects of the disclosure are directed to fabrication of the 3D SERS substrates comprised of vertically aligned ZnO nanowires, decoration with metal nanostructures, and immobilization of the capture anti-ADFP and anti-AQP1 on the surface of the metal nanostructures. The design of the SERS substrate (dimensions of the nanorods, spacing between the nanorods) may be optimized to maximize enhancement using AQP1 in buffer as an analyte. Aspects of the present disclosure are also directed to quantitative detection of ADFP and AQP1 in simulated (real) urine with known (unknown) concentration of AQP1 down to sub-ng/ml. The results are employed to build the SERS intensity vs. concentration calibration curve. Prototype SERS-based point of service assay are tested on patient samples to determine if quantification is identical to that of standard ELISA assay.

Aspects of the disclosure provide a novel plasmonic biosensing platform based on metal nanostructures with imprinted artificial receptors for non-invasive and rapid screening of RCC. The label-free assay is based on the detection of AQP1 and ADFP proteins in the urine using LSPR and SERS as transduction platforms. One aspect of the disclosure includes fabrication of gold nanostructures with artificial anti-AQP1 and anti-ADFP on the surface. Accomplishing this aim involves synthesis of gold nanostructures (e.g. nanorods and bipyramids), immobilization of the proteins (i.e. templates) and polymerization and crosslinking of the functional monomer around the template followed by the removal of the templates. Another aspect of the disclosure includes quantitative understanding of the specific binding efficacy of the synthetic receptors using surface force spectroscopy. Atomic force microscopy (AFM) based surface force spectroscopic measurements is employed to probe the specific interactions between the synthetic anti-AQP1 and target biomolecules by functionalized AFM tips. The measurements will provide a valuable insight into various parameters (e.g. choice of monomers, thickness of the polymer layer, crosslinking density), which are critical for the design of the synthetic receptors. Natural monoclonal antibodies against the target proteins will be employed as controls to compare the binding efficiency of the synthetic receptors. Another aspect of the disclosure includes plasmonic biosensing of the target biomolecules at physiologically relevant conditions using a paper based platform. Metal nanostructures with synthetic receptors on the surface will be immobilized on paper substrates to perform LSPR and SERS measurements. Statistical data analysis is performed to demonstrate the detection of target biomolecules at physiologically relevant concentrations (sub-ng/ml) and compared to standard enzyme-linked immunosorbent assay (ELISA).

Surface plasmon involves the collective coherent oscillation of the conductive electrons at the interface of metal and dielectric materials. Based on the sensitivity of the surface plasmon resonance to the dielectric ambient and the enhancement of electromagnetic field in proximity to metal nanostructures, two important classes of plasmonic biosensors (LSPR and SERS) are being actively investigated. LSPR- and SERS-based biosensing platforms have enormous potential to provide highly sensitive, cost-effective and point-of-care diagnostic tools. However, the state of the art approach (i.e. using natural antibodies as capture agents) presents several impediments in translation of these sensors to the real-world. Aspects of the present disclosure address this issue by designing and synthesis of plasmonic nanostructures with built-in synthetic receptors on the surface using a molecular imprinting approach. These novel plasmonic nanostructures with biofunctionality enable highly sensitive and specific biosensors for rapid screening of RCC. Apart from their impact in diagnostics, the plasmonic nanostructures disclosed herein with synthetic antibodies can also have applications in photothermal imaging (targeted accumulation), photo-thermal therapy, targeted drug-delivery and even neutralization of other biomolecules.

Synthesis of Metal Nanostructures

Figure 3A:
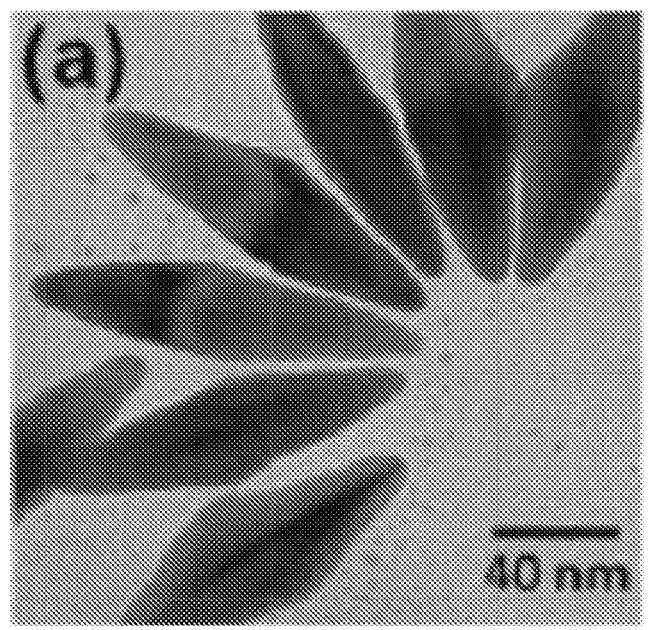
FIGS. 3a and 3b are TEM images of (a) gold bipyramids and (b) gold nanorods.
Figure 3B:
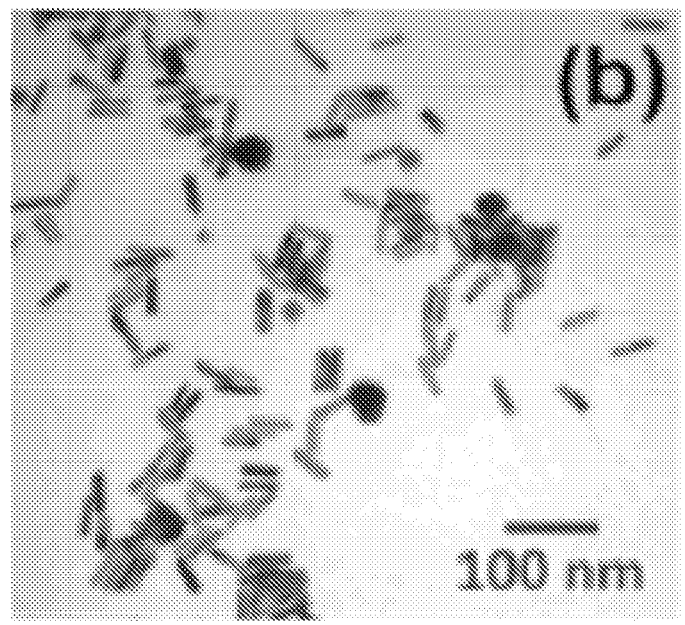

Owing to the sharp corners (electromagnetic hot spots) and facile tunability of the plasmon resonance by controlling the aspect ratio, gold nanorods and gold nanobipyramids are used for the fabrication of SERS substrates. The plasmon resonance wavelength half-way between the Raman source laser and Stokes-shifted Raman scattered light forms the ideal condition for maximum SERS enhancement. Gold nanorods and nanobipyramids are prepared using seed mediated approach, as described in more detail herein. FIGS. 3a and 3b show the TEM images of gold nanorods and nanobipyramids.

Figure 4A:
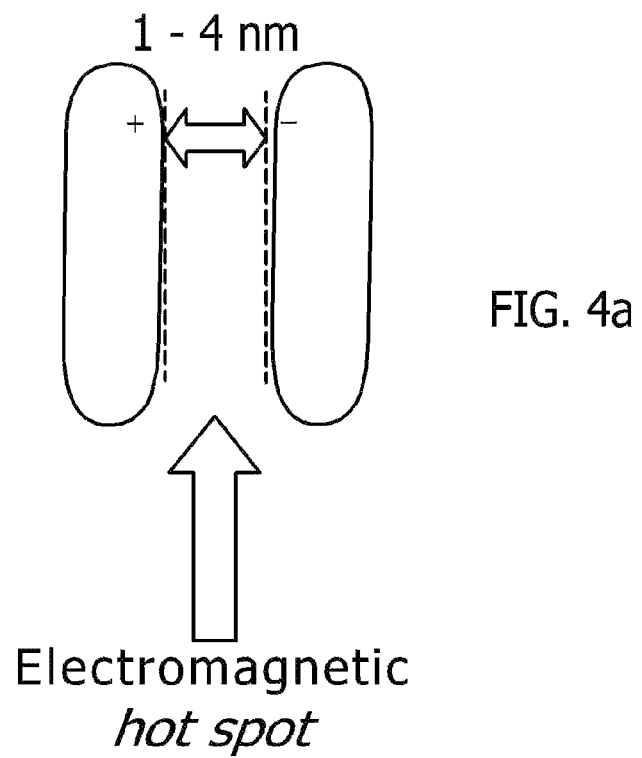
FIG. 4a is a schematic showing the SERS hot spot at the interstice of two nanopaticles.
Figure 4B:
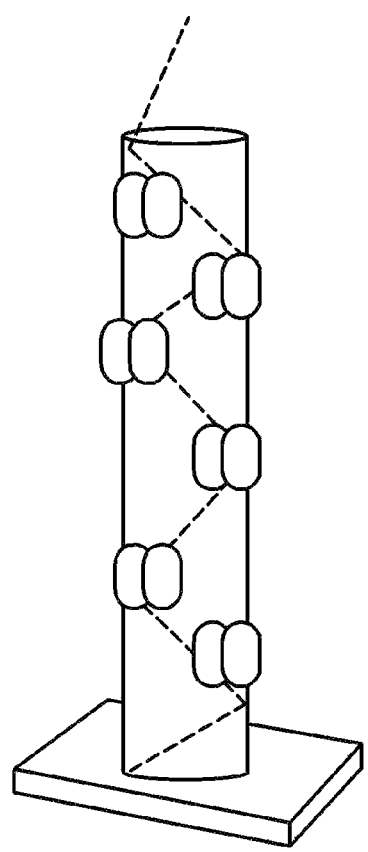
FIG. 4b is a schematic showing a ZnO nanorod decorated with nanoparticle dimers.

Efficiency of the SERS substrates can be enhanced by using dimers of gold nanorods and gold bipyramids instead of individual nanostructures (FIGS. 4a and 4b). The electromagnetic interaction (electromagnetic coupling) between metal nanostructures greatly increases the SERS intensity. In view of the large SERS enhancements from dimers and multi-particle aggregates, significant efforts have been made to chemically synthesize dimers and trimers of metal nanoparticles. A facile strategy, which involves a careful control of the amount of chloride added during synthesis of metal nanostructures to enable dimerization of metal nanostructures may be employed to form dimers of nanoparticles followed by their adsorption onto ZnO nanorods. One consideration in using dimers is the significant dependence of the electromagnetic enhancement on the polarization of light with respect to dimer axis. The SERS enhancement is maximized when the polarization is parallel to the dimer axis. The assembly of the dimers is tuned to orient the dimer axis parallel to the substrate by manipulating the drying (directional drying by tilting the substrate) of the nanoparticle solution on the vertically aligned nanowires (see FIG. 4b).

Synthesis of ZnO/Metal Nanostructure Hybrids

Figure 5:
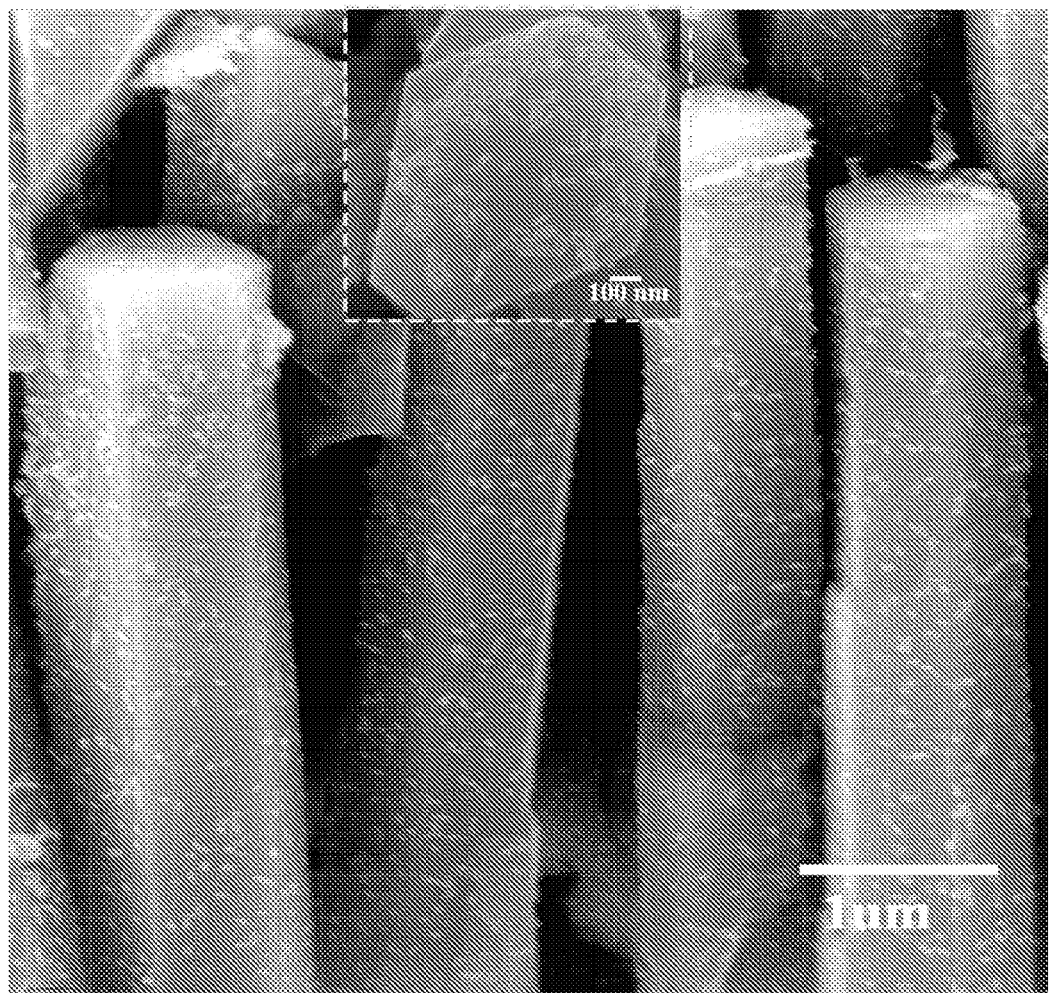
FIG. 5 is a SEM image showing the vertically aligned ZnO nanowires decorated with gold nanorods.

The ZnO nanowires may be grown using a solution approach in which ZnO seed layer (or gold with titanium adhesion layer) is deposited using magnetron sputtering or by spin casting zinc acetate solution on a silicon substrate (which can be replaced with a polymer or paper substrate at later stages). For the fabrication of vertically aligned ZnO nanowires, the substrates are exposed to a solution of zinc nitrate hexahydrate and hexamethylenetetramin. Substrates are subsequently rinsed with a mixture of ethanol and water and oven dried to result in uniformly oriented ZnO nanowires with a diameter of 100-300 nm and a length of 5-10 μm (see FIG. 5). The surface of the vertically aligned ZnO nanowires is modified with a monolayer of weak cationic polyelectrolyte, poly (2-vinyl pyridine) (P2VP) by adsorption from ethanol solution followed by extensive rinsing. One challenge for real-world application of the SERS as a biosensing platform is the ability to reliably and repeatedly quantify the analyte. Several factors which determine the uniformity of the envisioned SERS substrates are: (i) areal density of the vertically aligned ZnO nanowires, (ii) density of the nanoparticle or their aggregates decorating the ZnO nanowires, (iii) porosity (which determines the access to analytes) of the SERS substrate, and (iv) uniformity of the selective coating preferentially absorbing (or adsorbing) the analytes. Fabrication conditions influencing these various features may be identified and controlled to achieve a highly reproducible SERS enhancement within the substrate and from substrate to substrate.

Figure 2:
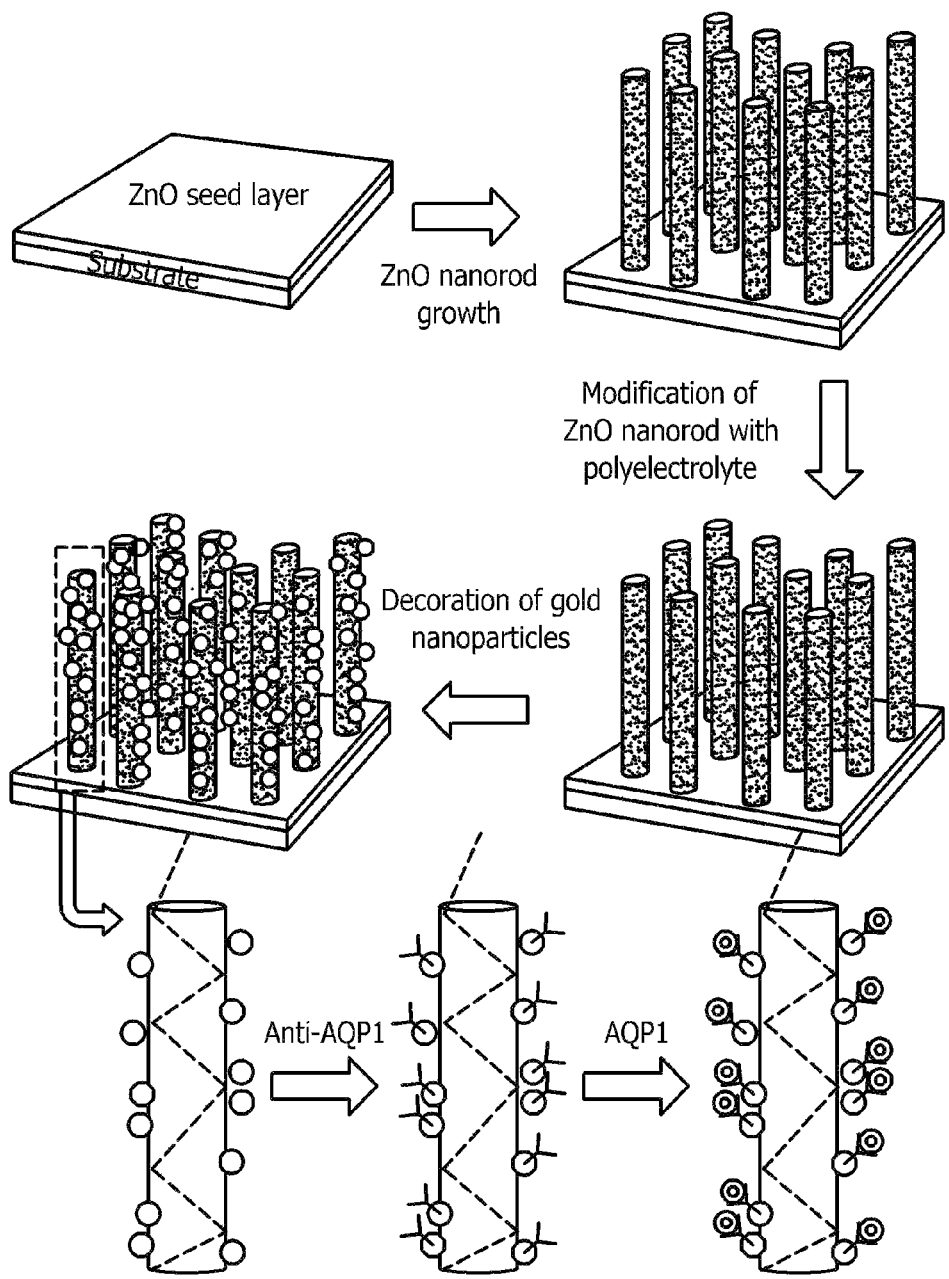
FIG. 2 is a perspective view of each of the steps of a fabrication routine for producing vertically aligned ZnO nanowires with gold nanoparticle arrays, and the waveguiding of light through the resulting ZnO/Au nanocob structure via multiple reflections.

Gold nanorods and gold nanobipyramids and their dimers are immobilized on the surface of the ZnO nanowires modified with P2VP, resulting in the vertically aligned hybrid nanostructures (see FIGS. 2 and 4). The next step involves the immobilization of the capture antibodies (anti-ADFP and anti-AQP1) on the gold nanostructures for selective binding of the target proteins. One consideration for the immobilization of the capture antibodies is retaining their ability to selectively capture target proteins. The capture antibodies are immobilized through protein A, which has specific affinity to gold and Fc fragment of the antibody. The immobilization protocol will involve the immobilization of protein A on the surface of metal nanostructures followed by immobilization of capture antibodies. Immobilization of capture antibodies and the functionality of the capture antibodies are verified by using fluorescently labeled target protein and monitoring the binding of these proteins to the capture biomolecules from buffered solution.

SERS Measurements and Statistical Data Analysis

Figure 6:
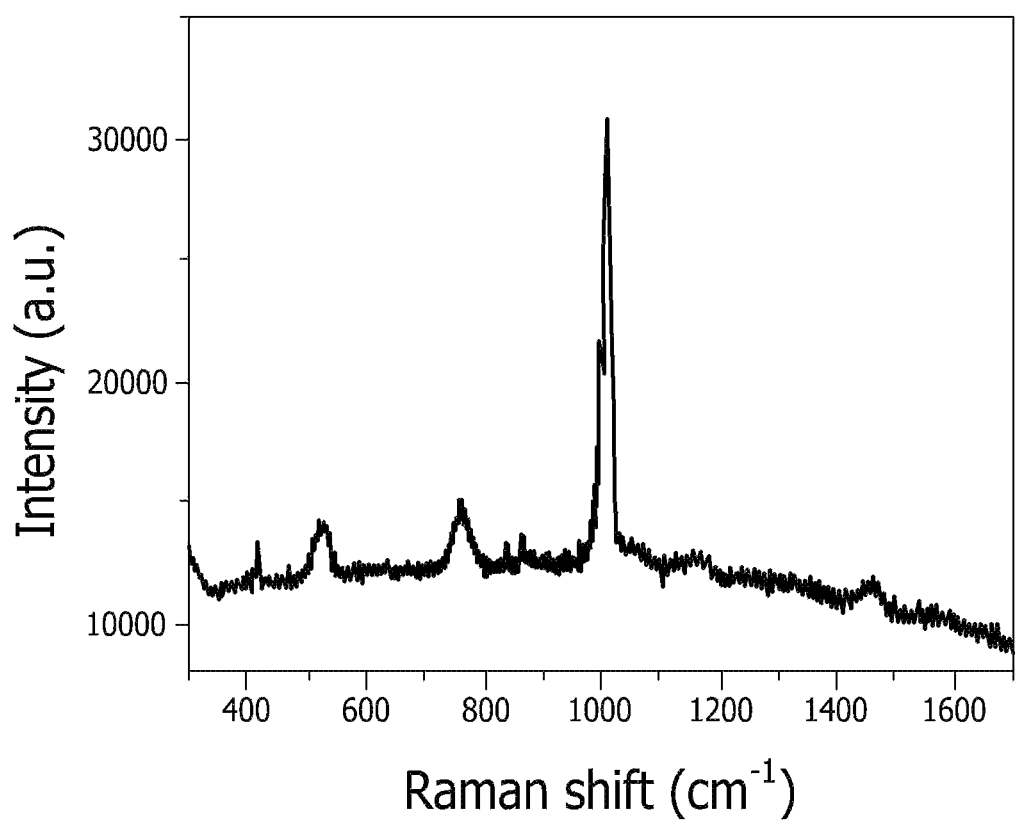
FIG. 6 is a graph of a SERS spectrum of adopophilin (1 mg/ml) on planar SERS substrate.
Figure 7A:
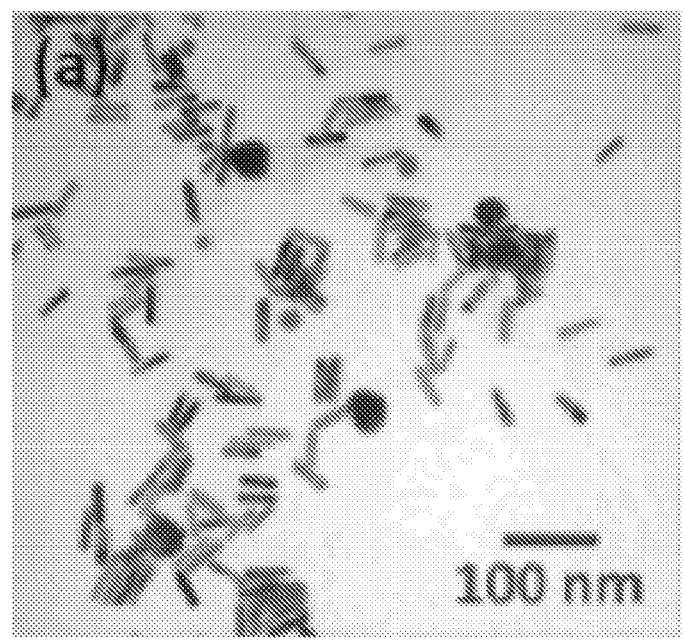
FIGS. 7a-7d are TEM images showing the extinction spectra of gold nanorods and nanobipyramids.
Figure 7B:
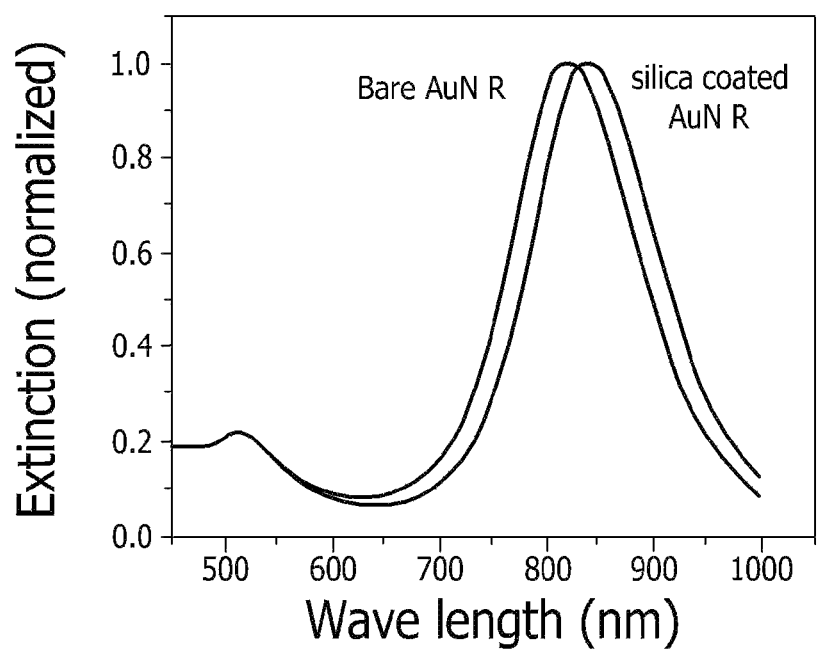
Figure 7C:
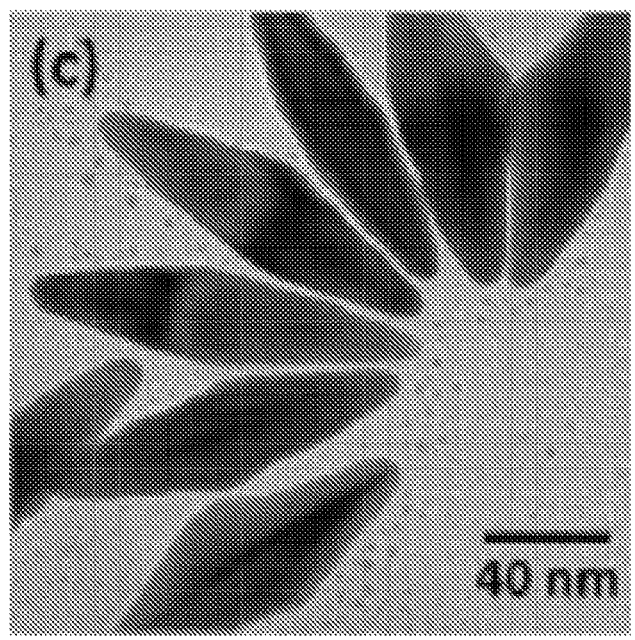
Figure 7D:
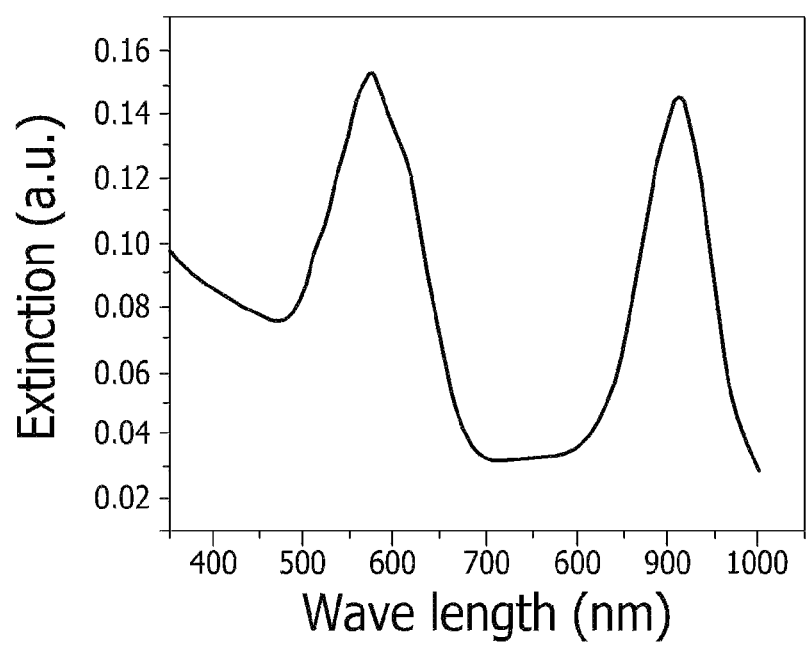

Characteristic Raman bands of AQP1, ADFP and the corresponding antibodies are identified using bulk Raman measurements or using conventional 2D SERS substrates and a high concentration of the biomolecules (1 mg/ml). The proteins are immobilized on metal nanostructure using histidine tag (hexa-histidine residues), which enables controlled appendage of the protein to the metal nanostructure with high regiospecificity. The imidazole ring of hisitidine adsorbs with flat-on geometry to the gold nanoparticle with high adsorption energy (~35 Kcal/mol). FIG. 6 shows the Raman spectrum of the his-tagged ADFP obtained by depositing the protein on planar SERS substrate. Raman spectrum clearly shows the strong characteristic bands of the protein. Following the identification of the Raman bands, the 3D substrates will be employed for detection and quantification of the target protein at trace levels (1 µg/ml-0.1 ng/ml). The hybrid nanostructures with capture antibodies will be exposed to various concentrations of the target proteins in buffered environment or in simulated urine followed by thorough rinsing to remove the non-specifically adsorbed protein. SERS spectra may be collected using a confocal Raman spectrometer mounted on a Leica microscope equipped with 514.5 and 785 nm lasers or a hand-held spectrometer. For 785 nm wavelength laser, which works well for gold nanostructures and biomolecules, the focal volume (and spot diameter) of the laser focused with 20× and 50× objectives is 32.3 fl (1.20 µm) and 2.61 fl (0.64 µm), respectively. The small spot size will enable probing individual ZnO nanowires and their ensemble. Furthermore, SERS and high resolution SEM can be obtained from the same location (even same nanowire) using external markers, which enable the correlation of the observed SERS intensity and the hybrid ZnO/metal nanostructure complex. This system and method of collecting SERS spectra data is merely exemplary, and it is contemplated that various other SERS spectra data collection methods and systems may be utilized within the scope of the claims.

The ability to distinguish similarly structured but different chemical species from a complex mixture of biological species using a spectral method requires a sufficient variability in the spectra of the species, and this variability should be greater than the variance due to inconsistencies that may arise from small differences in sample preparation. For moderate detection levels (concentration >1 µg/ml), SERS already provides distinct spectral differences due to the strong Raman bands, which are enhanced $10^5$-$10^9$ times compared to normal Raman scattering. However, at trace level detection (concentration <100 ng/ml), the spectral differences can be subtle for distinguishing the chemical species. To achieve the trace level analysis, multivariable statistical means, such as principal component analysis (PCA) via intrinsic Raman spectra of the analyte of interest, may be employed. Specifically, linear multivariable models of SERS spectra data sets may be built by establishing principal component vectors (PCs), which will provide the statistically most significant variations in the data sets, and reduce the dimensionality of the sample matrix. This approach involves assigning a score for the PCs of each spectrum collected followed by plotting the spectrum as a single data point in a two-dimensional plot. The plot will reveal clusters of similar spectra, thus individual biological species (analyte and interfering molecules) can be classified and differentiated for even closely related ones.

Example Comparison of 3D SERS Assay with Standard ELISA Assay

Two patient cohorts providing banked urine samples are provided. The first consists of 67 patients with histology-proven clear cell and papillary kidney cancer. Tumor size ranges from 0.6 to 18 cm with most being in the T1a stage of up to 4 cm. The second cohort consists of 54 control patients having surgery for non-kidney related issues that are matched by age, sex, weight, and smoking tendency to the kidney cancer patients. Obesity and smoking, both prevalent in the military, are risk factors for kidney cancer. AQP1 and ADFP levels are quantified in the real urine samples using the SERS approach and standard ELISA assay. The correlation between the concentrations of the proteins obtained from these independent techniques are analyzed using partial least squares (PLS) method. A standard commercial PLS package (e.g., PLS Toolbox) is employed for performing the statistical analysis to compare SERS assay with the gold standard (ELISA).

Nanoparticle Construction

Owing to their high refractive index sensitivity and facile tunability of the plasmon bands, gold nanorods (~250 nm/RIU) and gold nanobipyramids (~600 nm/RIU) are used as plamonic nanostructures. FIGS. 7a-7d show the TEM images and the extinction spectra of gold nanorods and nanobipyramids.

Example Construction of Gold Nanorod on Paper

Figure 8A:
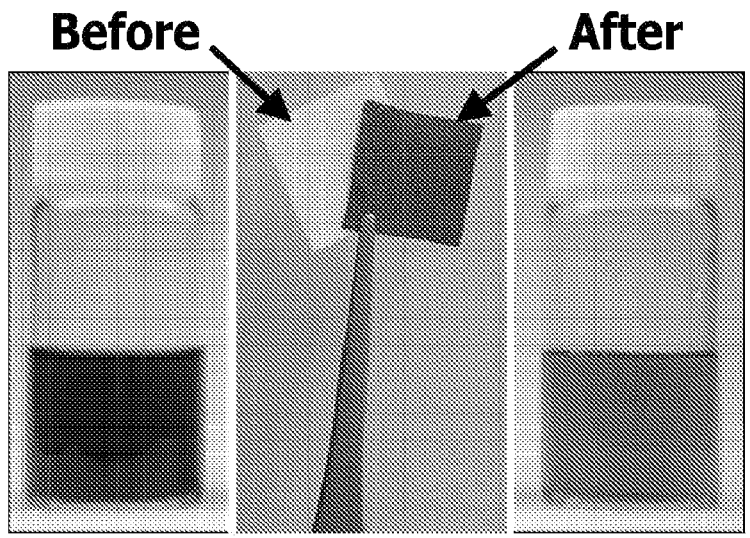
FIGS. 8a and 8b illustrate photographs of the AuNR solutions and the filter paper before and after exposure showing the strong color change, and UV-vis extinction spectra of the AuNR solution and the AuNR loaded paper showing the transverse and longitudinal plasmon absorption of the AuNR.
Figure 8B:
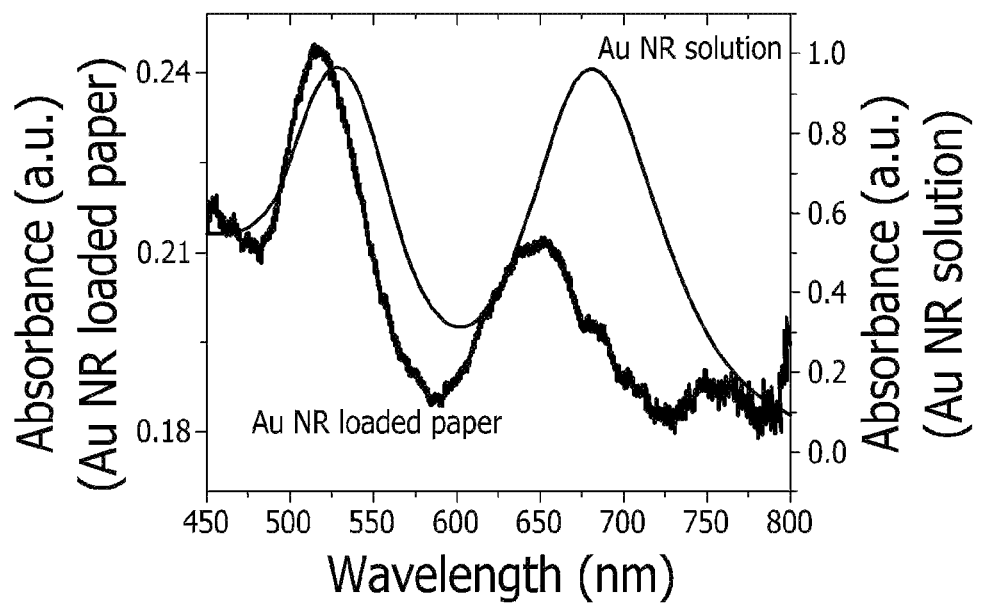

According to one aspect of this disclosure, gold nanorods were synthesized using a seed-mediated approach using cetyltrimethylammonium bromide (CTAB) as a capping agent, as described in more detail herein. The nanorods were found to be ~80 nm long and ~20 nm in diameter, making the aspect ratio to be nearly four. Exposing the filter paper to CTAB-capped gold nanorod solution resulted in uniform adsorption of the nanorods on the surface of the paper and a color change from white to purple (FIG. 8a). A significant decrease in the intensity of the purple color of the AuNR solution was observed after removing the paper from the solution (see FIG. 8a), which corresponded to nearly 50% decrease in extinction intensity. This significant change in the intensity of the color of the solution following the filter paper exposure is in accordance with the high density of nanorods on the surface of the paper and deep purple color of the paper. UV-vis extinction spectra of the AuNR solution showed the two characteristic peaks at ~530 nm and 650 nm corresponding to the transverse and longitudinal plasmon resonances of the nanorods, respectively (see FIG. 8b). AuNR loaded paper exhibited similar extinction spectrum with both transverse and longitudinal plasmon slightly blue shifted compared to the solution. The blue shift observed can be attributed to the change in the dielectric ambient (from water to air+substrate) with an effective decrease in the refractive index. The blue shift of the longitudinal plasmon peak (34 nm) was found to be slightly higher compared to the transverse band (12 nm), which can be attributed to the higher sensitivity of the longitudinal plasmon resonance to the changes in the dielectric ambient compared to the transverse band.

Figure 9A:
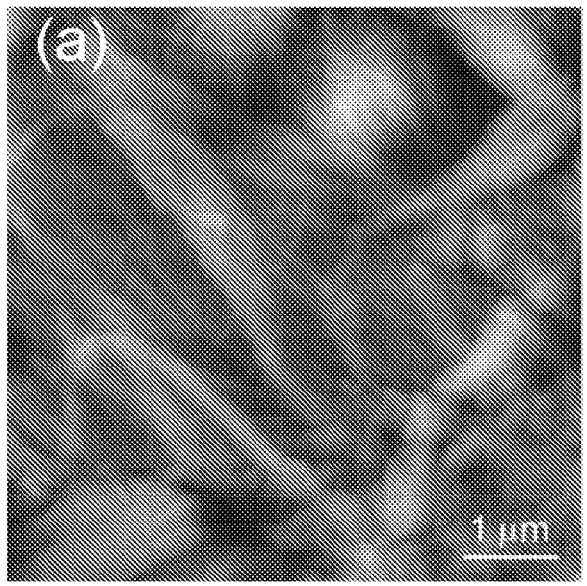
FIGS. 9a-9f are AFM images of a paper substrate with and without nanorods, an SEM image of nanorods, and an EDX image showing gold on the surface of the paper substrate.
Figure 10:
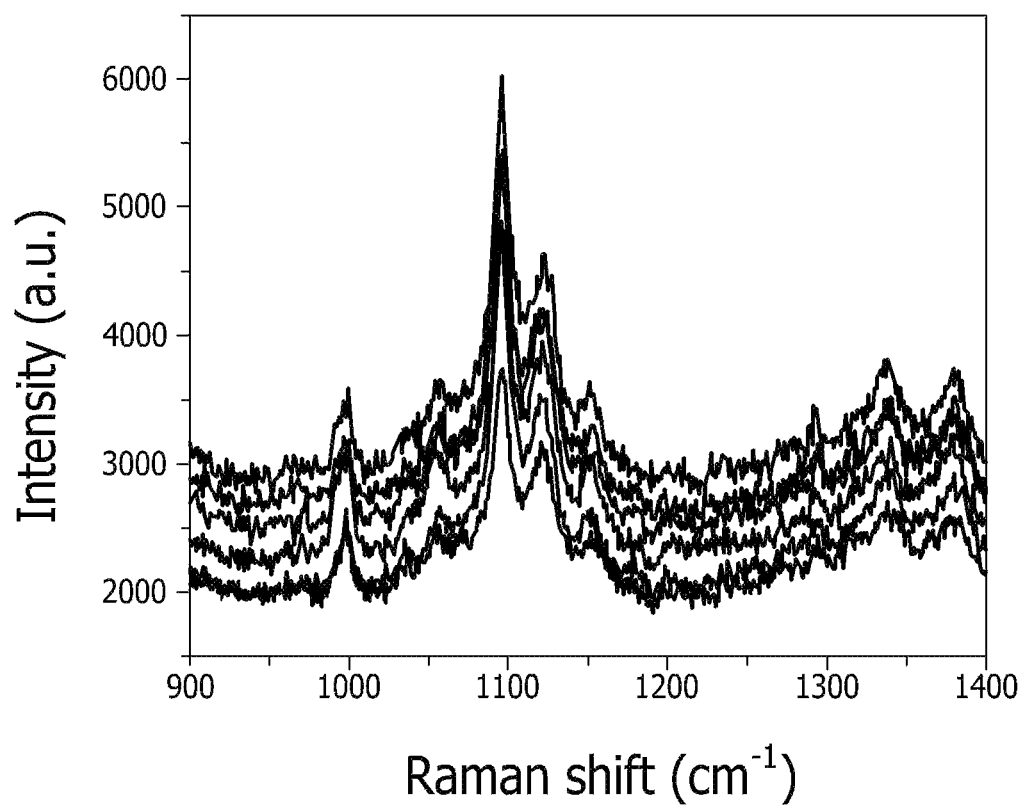
FIG. 10 shows the Raman spectra of filter paper collected at six different locations showing the remarkable uniformity of paper.

Cellulose is biodegradable, renewable, and abundant in nature thus cellulose (or paper) based products can be inexpensively produced and recycled. Due to numerous advantages such as significant reduction in cost, high specific surface area, excellent wicking properties, and compatibility with conventional printing approaches (enabling multiplex detection and easy disposability) paper is gaining increased attention as a substrate in diagnostic and tissue engineering applications. According to one aspect of this disclosure, paper may be constructed from cellulose fibers. Alternatively, or additionally, paper, or a fibrous mat, may be constructed from other materials, including woven and/or non-woven fibers (e.g., polymer fibers) and used as a substrate. FIG. 9a shows the hierarchical fibrous morphology of the filter paper with cellulose nanofibers braided into microfibers (average diameter of ~0.4 μm). The RMS surface roughness of the paper was found to be 72 nm over 5×5 μm² area, which indicates the large surface area of the paper substrates. Raman spectra obtained from six different areas of the pristine filter paper with 1 inch diameter exhibited excellent compositional (spectral) homogeneity, which may be important for its application as a SERS substrate (see FIG. 10). It is well known that uniform and high density adsorption of CTAB (cationic surfactant) capped AuNR to polymer surfaces is a significant challenge. It may be observed that once the AuNR loaded paper was dried, even under vigorous rinsing with water or alcohol, no noticeable change in the AuNR density was observed, suggesting the stability of these substrates for deployment in liquid environments. Cellulose has a large number of hydroxyl groups, which are accessible for attaching positively charged species. The uniform, irreversible, and high density adsorption of the AuNR is possibly due to the electrostatic interaction between the positive charged nanorods and the filter paper.

Figure 9B:
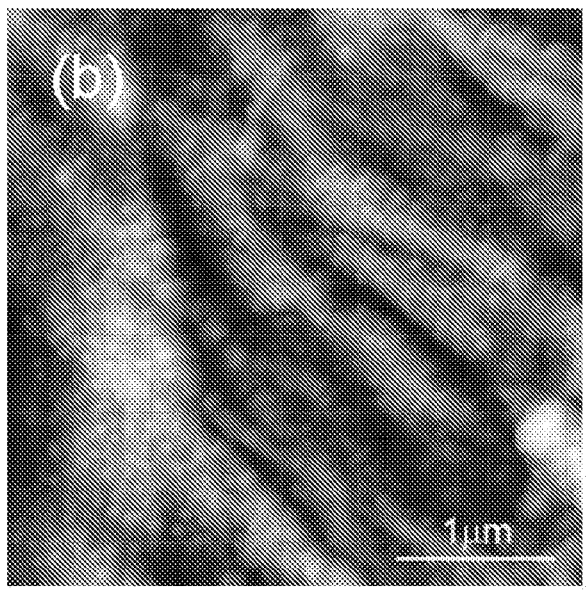
Figure 9C:
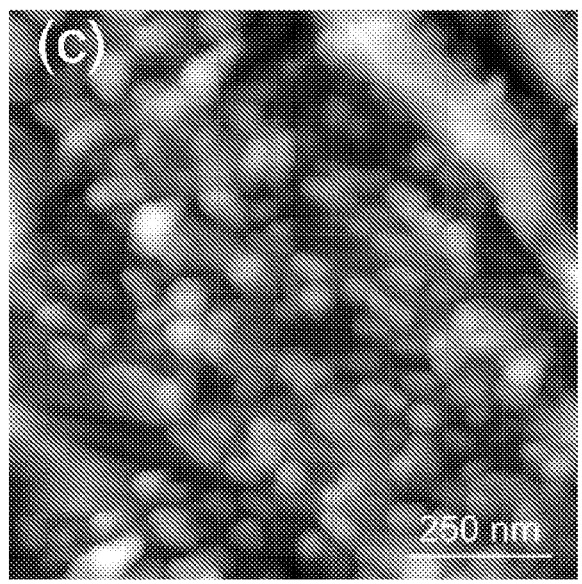
Figure 9D:
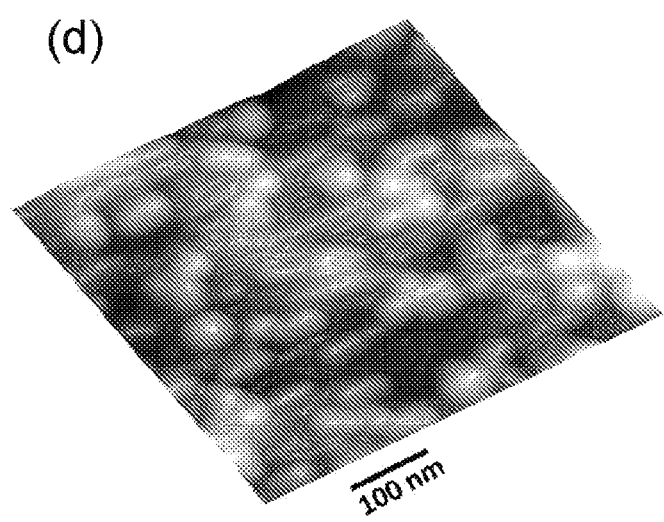
Figure 9E:
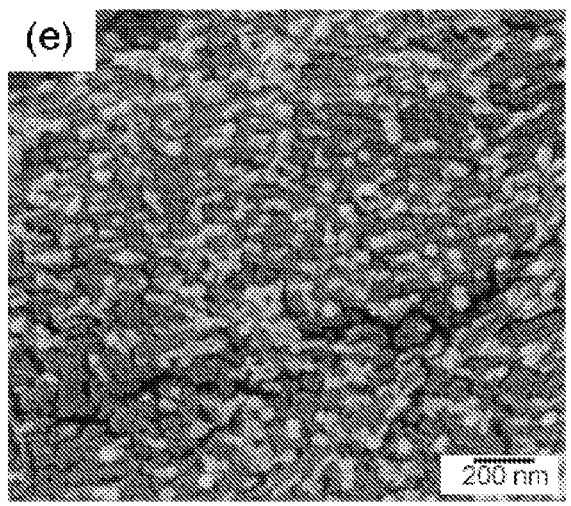
Figure 9F:
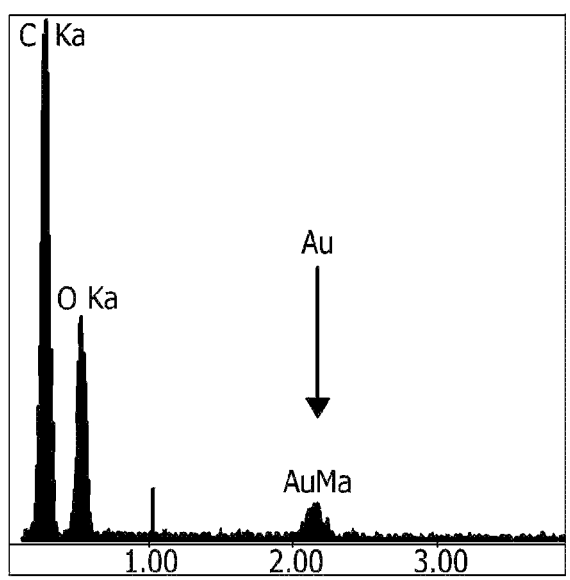

AFM imaging revealed a uniform and dense adsorption of nanorods on the surface of the paper without any signs of large scale aggregation of the nanorods (FIG. 9b). Higher magnification AFM images show the nanorods decorating the fibers of the paper and a partial local alignment of the nanorods along the nanofibers (FIGS. 9c, 9d). From numerous AFM images collected at different areas of the substrate, the number density of the nanorods was found to be 98±22/μm². High magnification SEM image shows the uniformly adsorbed gold nanorods on the paper (FIG. 9e). Energy dispersive X-ray spectra (EDX) confirmed the presence of gold on the surface apart from the carbon and oxygen rich cellulose fibers (see FIG. 9f).

Figure 11:
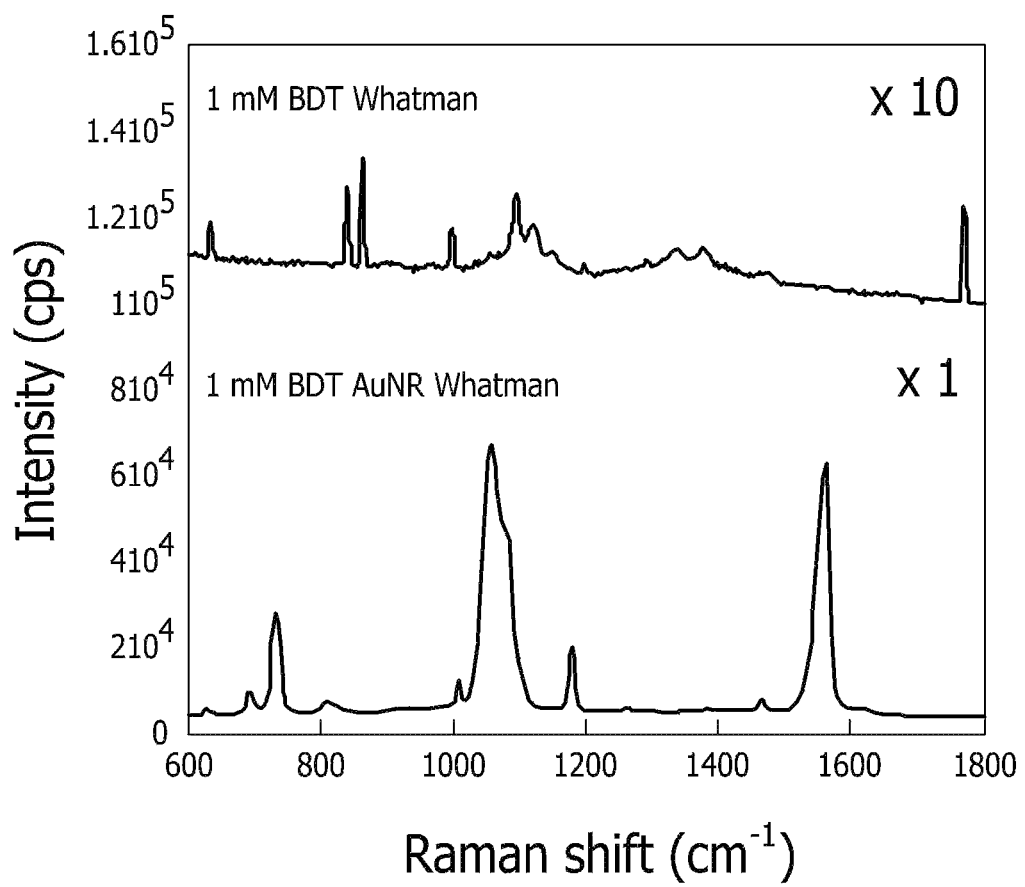
FIG. 11 shows the Raman spectra of pristine filter paper and filter paper loaded with AuNRs, both treated with 1 mM of 1,4-BDT.

1,4-Benzenedithiol (1,4-BDT) is widely employed as a model analyte for SERS owing to its ability to readily adsorb on gold or silver particles and its distinct Raman fingerprint. The Raman spectrum of 1,4-BDT in neat solid state exhibits strong bands at 740, 1058, 1093, 1186, and 1573 cm-1. Three prominent bands: 1058 cm-1 due to the combination of the phenyl ring breathing mode, CH in-plane bending, and CS stretching, 1181 cm-1 due to CH bending, and 1562 cm-1 due to phenyl ring stretching are commonly employed as characteristic peaks for evaluating the performance of SERS substrates. The 1058 cm-1 band was utilized to test the performance of the SERS substrate in detecting trace amounts of 1,4-BDT in ethanol. The pristine SERS substrate (AuNR loaded paper) does not show any peak in this region (see FIG. 11).

Figure 12A:
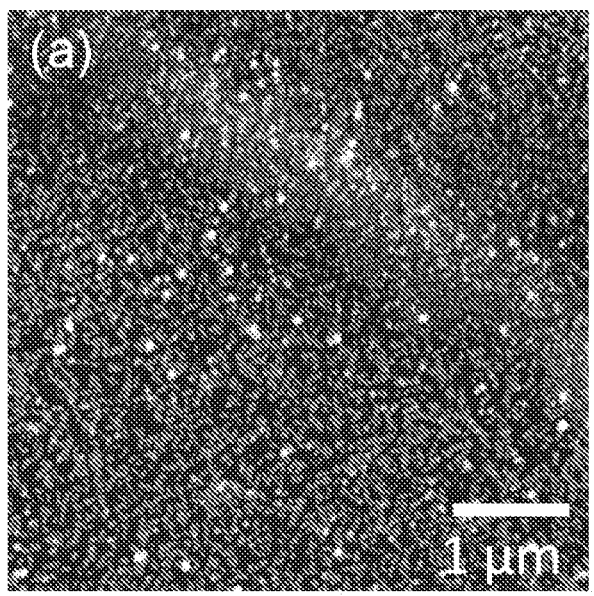
FIGS. 12a and 12b are AFM images of nanorods on a silicon surface modified with poly (2-vinyl pyridine).
Figure 12B:
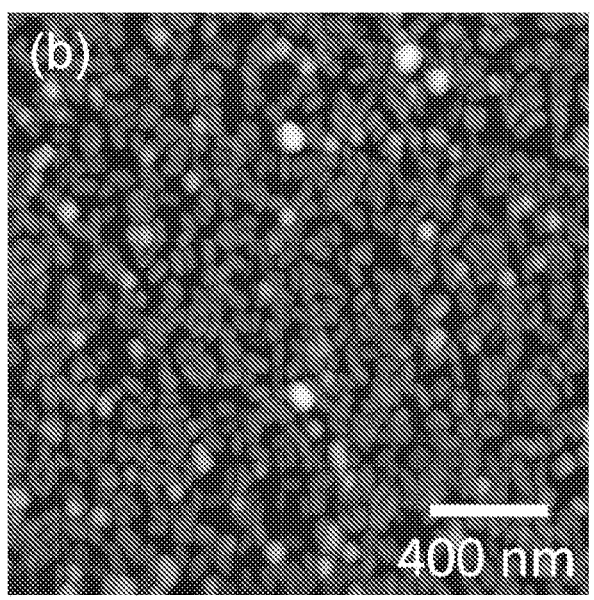

As a planar rigid substrate for comparison, a highly dense (number density: 220±14/μm²) layer of gold nanorods bound to silicon substrate modified with poly(2-vinyl pyridine) was employed (FIG. 12). FIG. 13 shows the Raman spectra obtained from the planar AuNR control sample and AuNR loaded paper both exposed to 1 mM of 1,4-BDT, followed by rinsing with ethanol. While the Raman spectra obtained from the AuNRs on silicon substrate exhibits weak Raman bands of 1,4-BDT, the AuNR loaded paper exhibited much stronger (~250 times) Raman bands. These Raman spectra obtained from the SERS substrates exhibited small shifts in frequency of the vibrational bands compared to the bulk 1,4-BDT (i.e. 1185 cm-1 for bulk BDT, and 1180 cm-1 for SERS substrate), possibly due to the orientation change of 1,4-BDT molecules adsorbed on to the AuNR.

Figure 13A:
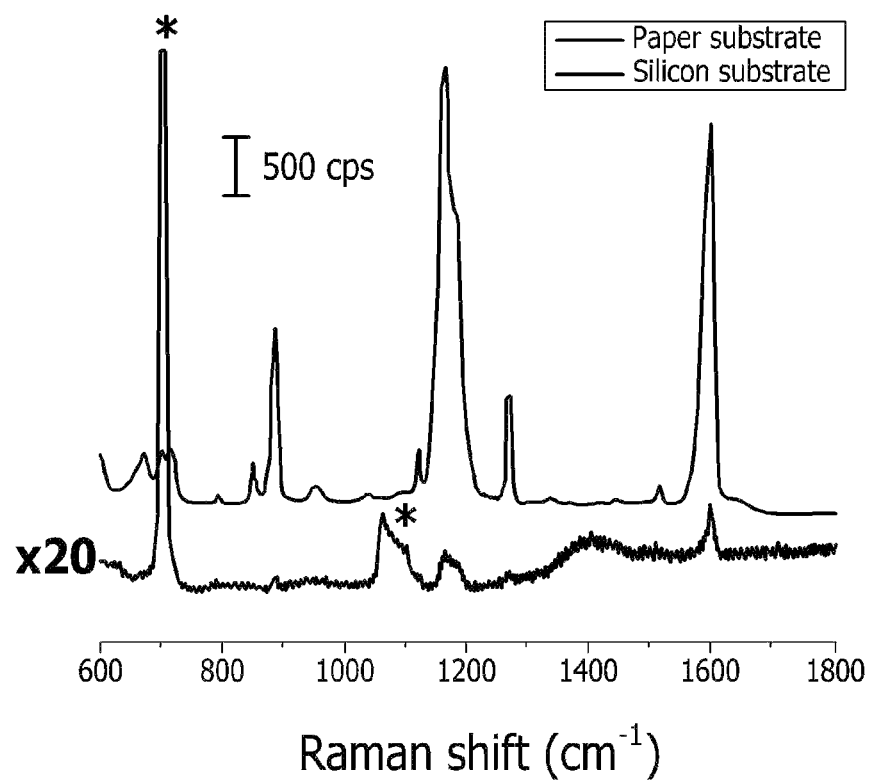
FIGS. 13a-13e show Rama spectra collected from AuNR loaded paper.
Figure 13B:
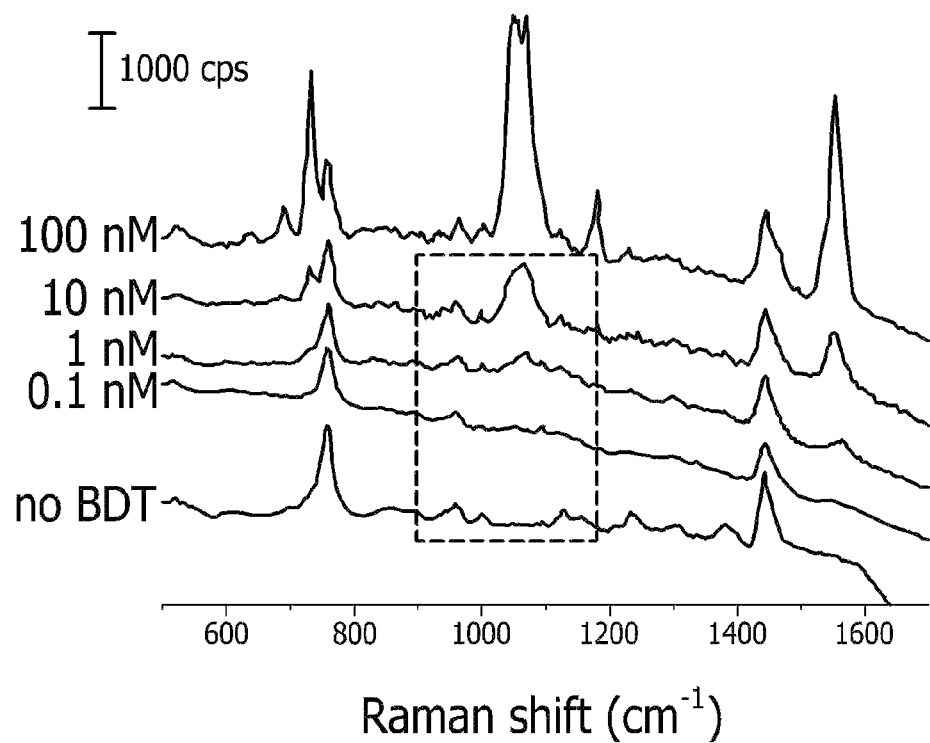
Figure 13C:
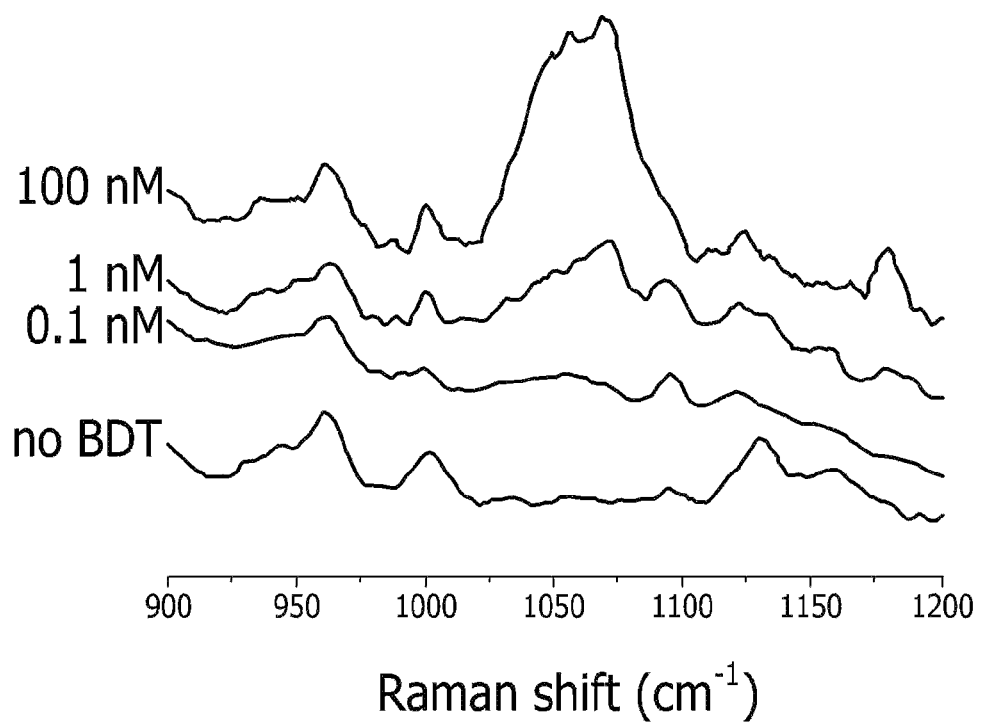
Figure 13D:
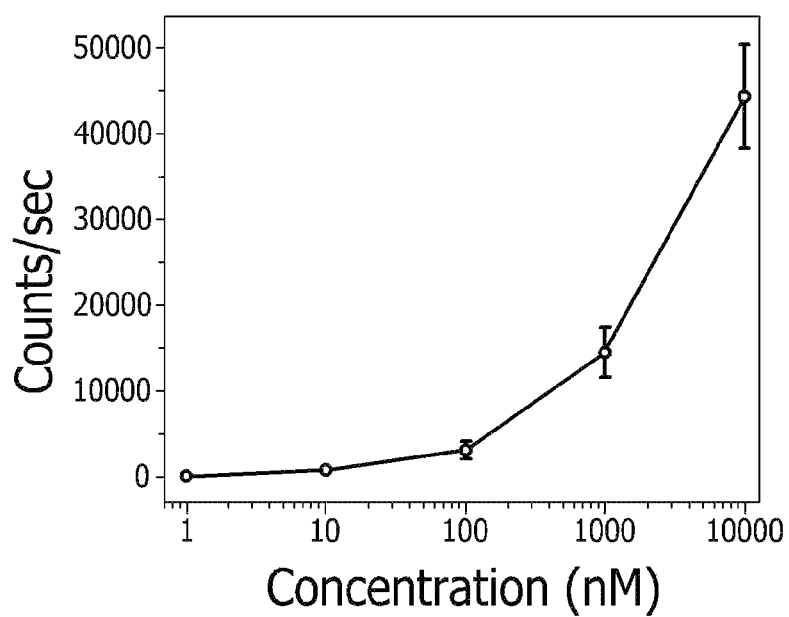
Figure 13E:
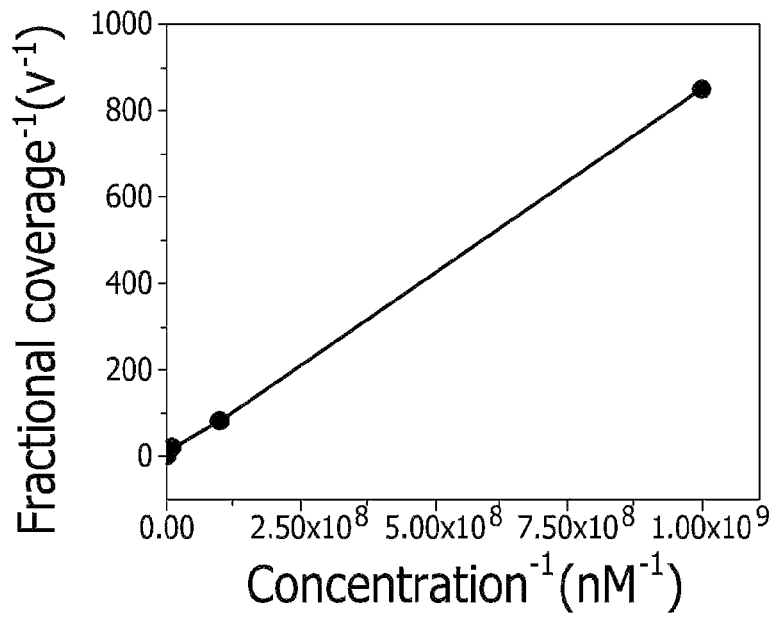
Figure 14A:
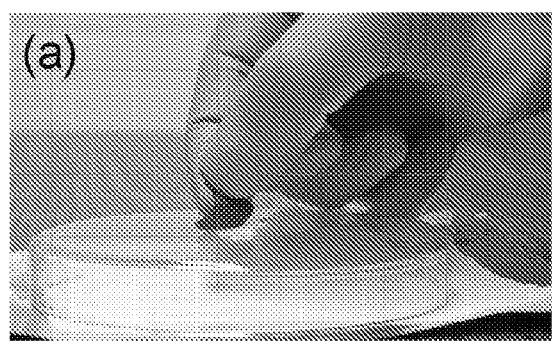
FIGS. 14a-14c show a paper-based SERS substrate being swabbed on a glass surface to collect trace amounts and SERS spectra.

To investigate the trace detection ability of the paper based SERS substrate, Raman spectra were collected from substrates exposed to 1,4-BDT down to concentrations of 0.1 nM. All the characteristic bands of the 1,4-BDT exhibited a monotonous decrease in intensity with decreasing concentration (FIG. 13b). FIG. 13c shows the higher resolution spectra of the smoothed 1058 cm-1 band, which is clearly distinguishable (signal to noise ratio of 3) down to a concentration of 0.1 nM (17 ppt) (see FIG. 14, illustrating higher resolution spectra). Semi-log plot of the concentration vs. 1058 cm-1 peak intensity shows a monotonic increase in the Raman intensity with increasing concentration of the analyte (FIG. 13d). Data from FIG. 13d can be plotted as the inverse of the fractional coverage (taken as a ratio of intensity, Imax/I) with respect to the inverse of the concentration (1/c), which exhibits a linear relationship, reflecting the expected Langmuir adsorption isotherm of 1,4-BDT to gold nanorods (see FIG. 13e).

The following expression was used to calculate the enhancement factor (EF) of SERS substrate at 1058 cm-1 band:

$$EF = I_{SERS} \times N_{bulk} / I_{bulk} \times N_{SERS} \tag{1}$$

where ISERS (NSERS) and Ibulk (Nbulk) are the intensities (the number of 1,4-BDT molecules probed) for the SERS and bulk spectra, respectively. NSERS was estimated by assuming a complete monolayer of 1,4-BDT on the nanorods for SERS substrates exposed to 1 mM concentration, which ensures that the enhancement factor is not overestimated. Based on numerous AFM images, the areal coverage of the AuNR was estimated to be ~23% and NSERS was calculated to be 4.9×105 molecules. Ibulk and Nbulk were determined from the Raman spectra of a 0.1 M of 1,4-BDT in 12 M NaOH(aq) (see experimental for details). Using the SERS intensity of the 1058 cm-1 band, the enhancement factor was calculated to be ~5×106. The enhancement factor observed here is high considering the absence of any resonance contribution, the use of gold nanostructures as opposed to silver nanostructures, which result in higher enhancement at the expense of poor long-term stability, absence of any intentionally formed hot spots (dimers or controlled aggregates) and the simplicity of the fabrication approach.

Figure 14B:
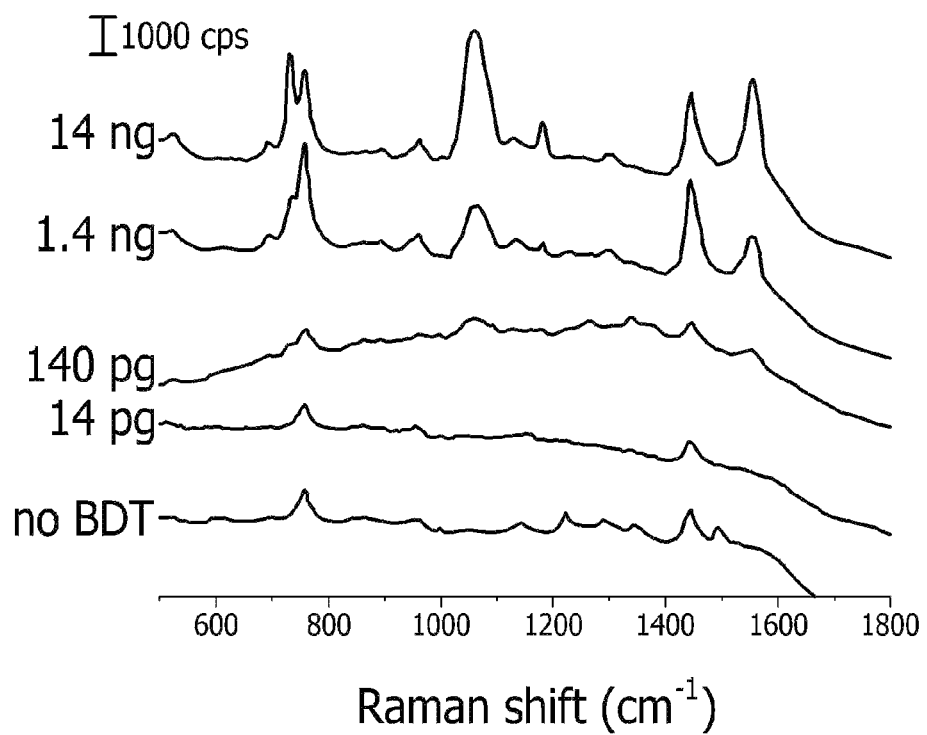
Figure 14C:
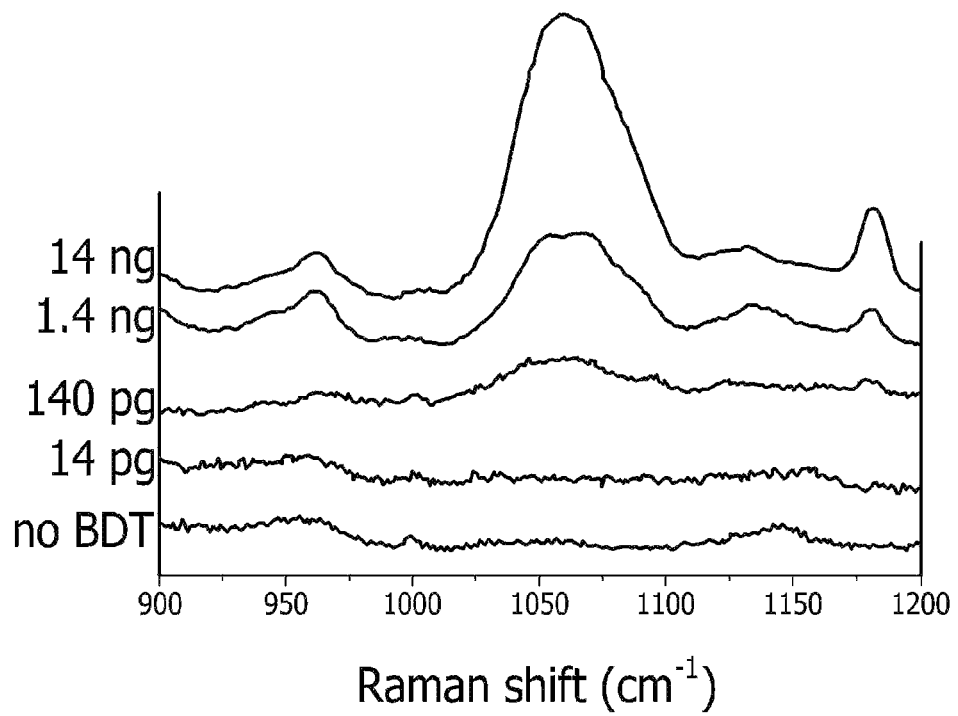

One of the distinct advantages of the paper based SERS substrate is the ability to collect trace amount of analytes from real-world surfaces by swabbing across the surface. This unique ability of the paper substrates is demonstrated by swabbing a slightly wetted (in ethanol) paper on surface of a glass with trace quantities of analyte deposited on the surface (see FIG. 14a). FIG. 14b shows the Raman spectra (averaged over 6 different spots) obtained by swabbing the paper across the surface with different amounts of analyte. Again, the strongest Raman band at 1058 cm-1 was used to evaluate the efficiency of the SERS swab. It can be seen that the Raman bands of 1,4-BDT can be clearly distinguished down to 140 pg on the surface (FIG. 14c). Considering that the swabbing of the surface results only a fraction of the analyte to be absorbed into the paper, a detection limit on the order of few tens of picograms on the surface is truly remarkable.

Envisioned and designed as an end-user level SERS substrate, proper handling of paper SERS substrate becomes an important issue as they contain metal nanostructures, which could be potentially harmful to humans and the environment. Toxicity of gold nanoparticles is still debated even though many reports indicate that gold nanoroparticles are essentially nontoxic. In a recent perspective, it was suggested that the toxicity and cell uptake of gold nanorods can be controlled to a point that they would not pose a serious harm by functionalizing the surface of gold nanorods with biocompatible ligands. A similar approach (i.e., tailoring the surface chemistry of the metal nanostructures) may be employed to make the paper SERS substrates bio-friendly.

Experiment: Gold Nanorod on Paper

Gold nanorods had been synthesized using a seed-mediated approach.25,26 Seed solution was prepared by adding 1 mL of an ice-cold solution of 10 mM sodium borohydride into magnetically stirred 10 mL of 0.1 M cetyltrimethylammonium bromide (CTAB) and 2.5×10-4 M HAuCl4(aq) solution at room temperature. The color of the seed solution changed from yellow to brown. Growth solution was prepared by mixing 95 ml of 0.1 M CTAB, 1 ml of 10 mM silver nitrate, 5 ml of 10 mM HAuCl4, and 0.55 ml of 0.1 M ascorbic acid in the same order. The solution was homogenized by gentle stirring. To resulting colorless solution, 0.12 ml of freshly prepared seed solution was added and set aside in dark for 14 hours. The solution turned from colorless to violet brown with most of the color change happening in the first hour. Prior to use, the gold nanorod solution was centrifuged at 13,000 rpm for 10 min to remove excess CTAB and redispersed in nanopure water (18.2 MΩ-cm). The procedure was repeated twice. AuNRs are loaded in a laboratory filter paper (Whatman No. 1 grade) by immersing a 1 cm2 paper in 2.5 mL of AuNR solution for two days. Upon removing from the solution, the paper was gently rinsed with nanopure water and then blow-dried under a stream of dry nitrogen. Planar silicon substrates for comparison were fabricated by modifying the silicon substrate with poly(2-vinyl pyridine) (P2VP) by exposing the piranha cleaned silicon surface to 4% P2VP solution in ethanol. After rinsing the silicon substrate with ethanol it was exposed to gold nanorod solution to enable adsorption of the gold nanorods. Finally, the substrate was rinsed with water to remove the loosely bound nanorods leaving a highly dense layer of nanorods on the surface.

For the dipping test, the performance of detecting a trace amount of 1,4-BDT was evaluated by dipping the SERS substrate in various concentrations of 1,4-BDT in ethanol for 20 minutes, followed by light rinsing with ethanol and drying with compressed nitrogen gas before the Raman measurements. Six Raman scans were performed for each substrate with each scan representing a different spot within the same substrate. The Raman data were averaged and normalized against 1058 cm-1 band.

For the swabbing test, 100 µL of 1 µM to 1 nM 1,4-BDT (corresponding to approx. 14 µg to 14 pg) in ethanol was pipetted on the surface of a glass slide, which immediately spread over 4 cm2 area. Evaporation of ethanol left residue of 1,4-BDT. A drop of ethanol was placed on a 0.5×1 cm SERS substrate to wet, and then swabbed the surface of the glass slide to pick up the residue of 1,4-BDT. Raman spectra of the swabbed SERS substrate were collected on six different spots. The Raman spectra were averaged and normalized against 1058 cm-1 band.

Raman spectra were measured using a Renishaw inVia confocal Raman spectrometer mounted on a Leica microscope with 20× objective (NA=0.40) in the range of 100-3200 cm-1 with one accumulation and 10 s exposure time. A 785 nm wavelength diode laser (0.5 mW) coupled to a holographic notch filter with a grating of 1200 lines mm-1 was used to excite the sample. The following expression was used to approximate the laser spot size (1.2 µm in diameter)

$$w_0 = \frac{0.61 \times \lambda}{NA} \quad (2)$$

where $w_0$ is the minimum waist diameter for a laser beam of wavelength $\lambda$ focused by a objective with a numerical aperture NA. The focal volume ($\tau$) was approximated from the following expressions $$\tau = \left(\frac{\pi}{2}\right)^{1.5} w_0^2 z_0 \quad (3)$$

$$z_0 = \frac{2\pi w_0^2}{\lambda} \quad (4)$$

where $z_0$ is the focal depth.

SEM images were obtained using a FEI Nova 2300 Field Emission SEM at an accelerating voltage of 10 kV. AFM images were obtained using Dimension 3000 (Digital instruments) AFM in light tapping mode. UV-vis spectra were measured using a CRAIC microspectrophotometer (QDI 302) coupled to a Leica optical microscope (DM 4000M) and a Shimadzu UV-1800 UV-vis spectrophotometer.

Surface Force Spectroscopic Measurements

In order to probe the specific recognition capabilities of the molecular imprinted nanostructures, AFM based force spectroscopy measurements are performed. All the force measurements are performed in controlled aqueous environment (phosphate buffer, pH 7.4) using a standard fluid cell, eliminating the contribution of capillary forces in the observed adhesion force. Commercially available microfabricated cantilevers with integrated probes with a nominal radius of less than 10 nm and spring constant of 0.05-0.5 N/m may be employed. The shape of the AFM tips are determined by scanning gold nanoparticle (diameter of 5 nm) standard samples. Cantilever spring constants may be obtained using thermal tuning or spring-on-spring measurements. In the initial stages, surface force spectroscopic (SFS) measurements are performed on planar silicon substrates with imprinted polysiloxane film.

Numerous functionalization strategies have been developed to bind the protein molecules to the surface of the AFM tip, each with its own set of advantages and shortcomings The his-tag on the protein may be employed to absorb the protein to the gold coated AFM tip. His-tag enables the region specific binding of the protein to the surface gold. The his-tag on the protein may space the AQP1 from the surface of the tip to preserve the natural conformation, thus it significantly reduces the non-specific adsorption onto the tip and provides necessary orientation freedom.

LSPR and SERS Measurements

Paper based substrates may be employed for performing the LSPR and SERS measurements on the molecular imprinted metal nanostructures. Paper substrates are exposed to the molecular imprinted plasmonic nanostructure solution followed by extensive rinsing and drying. AFM and SEM are employed to quantitatively probe the density of the nanostructures and uniformity of the substrate over large areas. Subsequently, LSPR/SERS biosensing measurements are performed by exposing the paper to simulated physiological liquid with various concentrations of the target biomolecules (discussed below). Finally, AQP1 and ADFP levels are quantified in the real urine samples using the SERS approach and standard ELISA assay. The correlation between the concentrations of the proteins obtained from these independent techniques may be analyzed using partial least squares (PLS) method. Standard commercial PLS package (PLS Toolbox) will be employed for performing the statistical analysis to compare SERS assay with the gold standard (ELISA).

Artificial Antibodies on Gold Nanostructures

Two designs for integrating plasmonic biosensing (LSPR and SERS based approaches) with synthetic receptors using molecular imprinting disclosed herein involve surface imprinting of the artificial receptors onto the metal nanostructures. As disclosed herein, surface imprinting as opposed to the bulk imprinting offers distinct advantages in that the capture sites are readily available to the analyte molecules significantly reducing the sensor response time. Furthermore, considering the surface sensitive nature of the transduction chosen in this study (LSPR and SERS), bulk imprinting may not provide any additional advantages such as higher sensitivity or larger dynamic range. Two different surface imprinting strategies are described herein.

Molecular Imprinted Nanostructures

Figure 15:
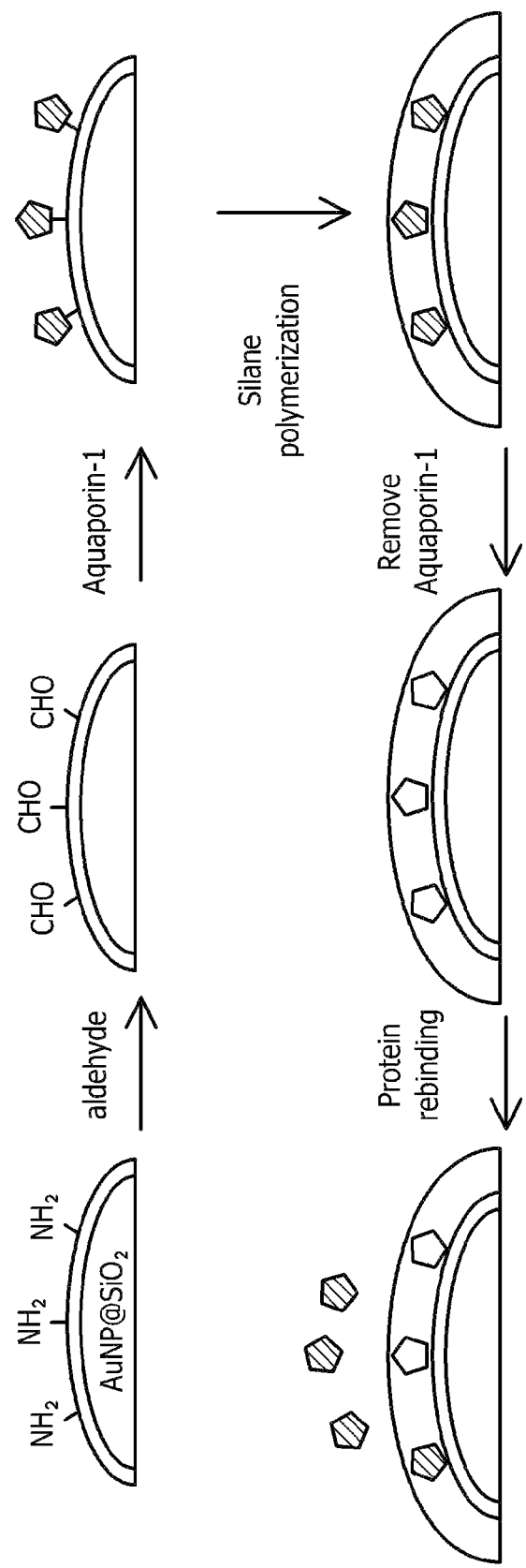
FIG. 15 is a flow chart of schematics showing the formation of the molecular imprinted plasmonic nanostructures using silane polymerization.

In one approach, silane polymerization is exploited to achieve molecular imprinted artificial antibodies on the surface metal nanostructures (see FIG. 15). The silane polymerization will be performed by sol-gel methods, where the polysiloxane networks are formed by siloxane bonds between silanol groups. The surface of the silica shells of AuNP@SiO2 (i.e., the silica-coated gold nanostructures) may be modified by introducing amine functionality using 3-aminopropyltrimethoxysilane (APTMS). Aldehyde functionality may then be introduced using glutaraldehyde where the amine groups on the silica surface are converted to aldehyde groups. Hemoglobin (or His-tagged AQP1 and his-tagged ADFP) may be bound to the surface of the AuNP@SiO2 using the aldehyde groups on the surface of these particles, forming imine bonds. Following the immobilization of the proteins on the surface of the metal-silica nanostructures, organic silane monomers, APTMS and propyltrimethoxysilane (PTMS) may be polymerized onto the hemoglobin-silica (or AQP-1-silica) surface at room temperature under buffered conditions to prevent the denaturing of the protein molecules. Concentration of PTMS below 60% facilitates the easy removal of the template molecules after the silane polymerization. The template may then be removed by washing with organic acid or acidic reagents such as oxalic acid. Oxalic acid breaks the imine bond between the silica surface and the protein, thus removing the proteins from the surface. The removal of the template leaves recognition cavities, which act as specific recognition sites for the rebinding of the protein. The schematic of the imprinting of protein onto silica surface is shown in FIG. 8. One of the challenges for reliable biosensing is overcoming non-specific binding of the biomolecules to the active sensing layer. The possibility of non-specific binding even in the case of the molecularly imprinted nanostructures is contemplated. The non-specific interactions may be too strong to overcome even with thorough washing with buffer solution. To overcome this issue, polyethylene glycol (PEG) may be used as a passivating layer. This can be achieved in two ways: (i) polysiloxane network will be formed using sliane monomers functionalized with PEG side chains or (ii) grafting PEG chains to polysioxane network before removal of the template molecules. PEG has been demonstrated to be efficient in preventing non-specific binding of the biomolecule and enhance the sensitivity of plasmonic sensors.

Surface Imprinting on Immobilized Particles

Figure 16:
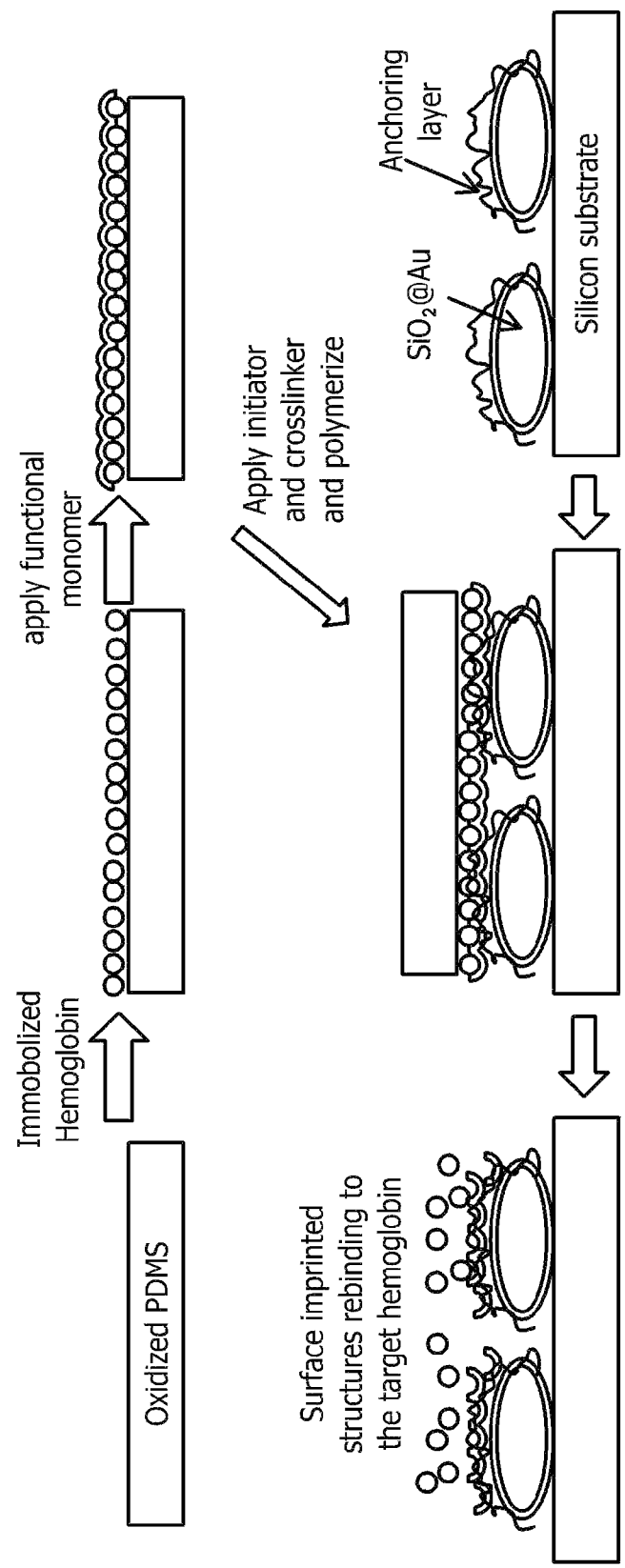
FIG. 16 is a schematic showing the molecular imprinting on the surface of the plasmonic nanostructures bound to the surface of a substrate.

In an alternate approach, surface molecular imprinting will be achieved using soft substrates, which can make conformal contact with metal nanostructures immobilized on the surface (see FIG. 16). The surface imprinting process will start by immobilizing hemoglobin onto oxidized polydimethyl siloxane (PDMS) substrates. Amination of the PDMS substrates will be performed by exposing the substrates to APTMS. Aldehyde groups for binding the hemoglobin to the surface of PDMS-NH2 will be formed by reacting with glutaraldehyde. Hemoglobin will be bound to the surface of the PDMS-NH2 with aldehyde groups forming imine bonds as described above. Successful immobilization of the hemoglobin will be verified by fluorescence (using labeled protein) and AFM. Following the immobilization of the protein on PDMS surface, a functional monomer such as metahcrylic acid (MAA), which possesses carboxylic groups, will be applied to the PDMS with hemoglobin. Following the assembly of the monomer around the protein by non-covalent interactions such as hydrogen bonding, excess monomer will be removed by gently washing in alcohol. Subsequently, the surface will be inked in crosslinker (divinyl benzene), radical initiator (benzylperoxide) and an anchoring monomer (triethoxyvinylsilane(TVES)) causing the polymerization of the functional monomer around the hemoglobin molecules. In the next step, PDMS substrate will be brought in conformal contact with the gold/silica core-shell nanoparticles immobilized on the surface of a substrate, followed by peeling the PDMS off to leave the molecular imprints on the surface of the nanostructures on the surface. The AuNP@SiO2 or Au NP will be immobilized on the surface of silicon substrate using poly(2-vinylpyridine) (P2VP) as an anchoring layer. Silicon surface will be modified with P2VP by adsorption from dilute solutions or by spin coating approach. The TVES layer will act as an anchoring layer for binding the imprinted receptors to the silica coated nanoparticles. In an alternate approach, polyglycidyl methacrylate (PGMA) may be employed as an anchoring layer for immobilization of the polymerized MAA receptors directly onto the gold nanoparticle immobilized onto the substrate. Owing to the sticky epoxy groups, PGMA exhibits excellent binding to a wide variety of organic and inorganic species.

Immobilizing Natural Antibodies on Gold Nanostructures

One of the considerations for the immobilization of the capture antibodies is retaining their ability to selectively capture target proteins. The capture antibodies may be immobilized through protein A, which has specific affinity to gold and Fc fragment of the antibody. The immobilization protocol may involve the immobilization of protein A on the surface of metal nanostructures followed by immobilization of capture antibodies. Immobilization of capture antibodies and the functionality of the capture antibodies may be verified by using fluorescently labeled target protein and monitoring the binding of these proteins to the capture biomolecules from buffered solution.

It will be understood that the particular embodiments described herein are shown by way of illustration and not as limitations of the disclosure. The principal features of this disclosure may be employed in various embodiments without departing from the scope of the disclosure. Those of ordinary skill in the art will recognize numerous equivalents to the specific procedures described herein. Such equivalents are considered to be within the scope of this disclosure and are covered by the claims.

An efficient SERS substrate based on common filter paper filled with gold nanorods is described herein, which exhibited more than two orders of magnitude higher SERS enhancement compared to the silicon based SERS substrate. Numerous favorable traits of the paper such as flexibility, conformability, efficient uptake, and transport of the analytes from liquid and solid media to the surface of metal nanostructures due to hierarchical vasculature and high specific surface area make the paper based SERS substrates demonstrated here an excellent candidate for trace chemical and biological detection. The paper based SERS substrates also offer cost-effective platform for SERS detection and opens up a new venue for other biological and chemical detection. The process demonstrated here can be easily scaled up for batch fabrication of SERS swabs. Furthermore, the paper-based SERS substrate introduces a novel platform for integrating conventional chromatography, microfluidics and biological assays (e.g Western blot analysis) with SERS, imparting chemical specificity to these techniques. Similar to microfluidic devices, paper SERS based multiplexed detection of analytes from a complex real-world sample can be a very powerful approach. Electrospinning of polymer fibers may also be a potential method for realizing flexible SERS substrates. Electrospun polymer mats possess a hierarchical fibrous structure similar to that of paper, and the use of different types of polymers in electrospinning can bring better control (fiber diameter, alignment, surface chemistry) and multi-functionality to the SERS design and applications.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present disclosure have been described in detail, it will be understood by those skilled in the art that various modifications can be made therein without departing from the spirit and scope of the disclosure as set forth in the appended claims.

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A surface enhanced Raman scattering sample collection and testing apparatus comprising:
    a fibrous substrate; and
    a plurality of surface enhanced Raman scattering nanoparticles, wherein the plurality of nanoparticles are metal nanorods, adhered to a surface of the fibrous substrate.

2. The apparatus of claim 1 wherein the fibrous substrate comprises a cellulous substrate.

3. The apparatus of claim 1 wherein the plurality of surface enhanced Raman scattering nanoparticles are gold nanorods.

4. The apparatus of claim 1 wherein the fibrous substrate is a natural fibrous material.

5. The apparatus of claim 1 wherein the fibrous substrate is a synthetic fibrous material.

6. A method of testing a surface for a target substance comprising:
    swabbing a surface with a surface enhanced Raman scattering sample collection and testing apparatus comprising:
        a fibrous substrate; and; a plurality of surface enhanced Raman scattering nanoparticles, wherein the plurality of nanoparticles are metal nanorods, adhered to a surface of the fibrous substrate; and performing Raman spectroscopy on a surface enhanced Raman scattering sample collection and testing apparatus.

7. The method of claim 6 wherein the target substance is at least one of a bacteria, a virus, a biological agent, a chemical agent, an explosive, and an explosive residue.

8. The method of claim 6 further comprising:
preparing a solution of nanoparticles;
submerging at least a portion of a cellulose substrate in the prepared solution of nanoparticles; and
removing the portion of the cellulose substrate from the prepared solution of nanoparticles.

\* \* \* \* \*